United States Patent [19]

Rüttimann

[11] Patent Number: 5,763,651
[45] Date of Patent: Jun. 9, 1998

[54] PROCESS FOR MANUFACTURING POLYENE ESTERS AND ACIDS

[75] Inventor: August Rüttimann, Arlesheim, Switzerland

[73] Assignee: Roche Vitamins Inc., Parsippany, N.J.

[21] Appl. No.: 865,289

[22] Filed: May 29, 1997

[30] Foreign Application Priority Data

Jun. 17, 1996 [EP] European Pat. Off. ............ 96109660

[51] Int. Cl.$^6$ .................... C07C 67/24; C07C 67/00
[52] U.S. Cl. .................... 562/509; 562/510; 562/598; 562/599
[58] Field of Search .................... 562/509, 510, 562/598, 599

[56] References Cited

U.S. PATENT DOCUMENTS 4,937,308  6/1990  Kraus et al. .................... 558/124

OTHER PUBLICATIONS

I. Fleming et al., Tetrahedron Letters, No. 34, pp. 3209–3212 (1979).
I. Fleming, Chimia 34, No. 6, pp. 265–271 (1980).
I. Paterson et al., Tetrahedron Letters 22, No. 29, pp. 2833–2836 (1981).
H. F. Chow et al., Tetrahedron Letters 26, No. 3, pp. 397–400 (1985).
Hertler et al., J. Org. Chem., vol. 53, (15), pp. 3532–3539 (1988).
Yamamoto, et al., J. Chem. Soc., Chem. Commun., pp. 1639–1640 (1988).

*Primary Examiner*—Jeffrey Mullis
*Attorney, Agent, or Firm*—George W. Johnston; William H. Epstein; John P. Parise

[57] ABSTRACT

A process for the manufacture of polyene esters or polyene acids comprises reacting a polyene O,O-dialkylacetal or di(O,O-dialkylacetal) with a vinylketene acetal or analogue thereof in the presence of a Lewis acid, hydrolyzing the reaction mixture depending on the vinylketene acetal used, subsequently cleaving alcohol under strongly basic conditions from the polyene derivative produced at this stage and, where the desired ester or carboxy group is still not present, performing the respective conversion. Certain intermediates in this process form a further aspect of the invention. The final products are primarily carotenoids which can be used appropriately, e.g. as colorants and pigments for foodstuffs, animal products etc.

9 Claims, No Drawings

PROCESS FOR MANUFACTURING POLYENE ESTERS AND ACIDS

BACKGROUND OF THE INVENTION

1. Field

The present invention relates to a novel process for manufacturing polyene esters and acids from acetalized polyene aldehydes via an acid-catalyzed condensation reaction with vinylketene acetals.

2. Description

Lewis acid-catalyzed additions of α,β-unsaturated ethers (enol ethers) to acetals have been known for a long time and date back to the work of Müller-Cunradi and Pieroh (see U.S. Pat. No. 2,165,962). Hoaglin and Hirsch [J.A.C.S. 71: 3468 (1949)] investigated this reaction further and broadened the possible applications, which Isler et al. likewise did in the 1950's with respect to the synthesis of β-carotene, crocetin dialdehyde, lycopene as well as β-apocarotenoids [see Helv. Chim. Acta, 39: 249 et seq. and 463 et seq. (1956), ibid., 42: 854 et seq. (1959) as well as U.S. Pat. Nos. 2,827,481 and 2,827,482]. Later, Mukaiyama [Angew. Chem., 89: 858 et seq. (1977) and Org. Reactions, 28: 203 et seq. (1982)] extended the reaction by using the readily accessible trimethylsilyl enol ethers.

The first Lewis acid-catalyzed condensations of 1-alkoxy-1,3-dienes (dienol ethers) with α,β-unsaturated acetals were reported by Nazarov and Krasnaya [J. Gen. Chem. USSR, 28: 2477 et seq. (1958)] and by Makin [Pure & Appl. Chem., 47: 173 et seq. (1976), J. Gen. Chem. USSR, 31: 3096 et seq. (1961) and 32: 3112 et seq. (1962)]. Here, the coupling of the acetal to the dienol ether takes place as far as can be seen exclusively at its γ-position with the formation of a chain-lengthened α,β-unsaturated acetal, which, however, in competition with the first acetal reacts with further dienol ether to form a further, chain-lengthened α,β-unsaturated acetal etc. [telomer formation; see also Chemla et al., Bull. Soc. Chim. Fr., 130: 200 et seq. (1993)]. For this reason such a condensation has been found unworkable for synthetic purposes, especially for the synthesis of apocarotenoids [Isler et al., Adv. Org. Chem., 4: 115 et seq. (1963)].

Not only 1-alkoxy-1,3-dienes, but also trimethylsilyloxy-dienes [of the type $CH_2=CH-CH=CH-OSi(CH_3)_3$] can be condensed with acetals in the presence of Lewis acid catalysts, as disclosed by Mukaiyama et al. in Chem. Lett. 1975, 319 et seq. In this coupling too the attack takes place exclusively at the terminal (γ-) carbon atom of the diene system in order to form "γ-products" [see Mukaiyama et al., Bull. Chem. Soc. Jap. 50: 1161 et seq. (1977) and Japanese Patent Publication (Kokai) 36,645/1977]. In contrast to the reaction with 1-alkoxy-1,3-dienes, in the case of the reaction of trimethylsilyloxydienes with acetals there is formed an aldehyde which does not react further with the diene (no telomer formation). By using this method Mukaiyama et al. were able to synthesize vitamin A [see Kokai, 36,645/1977, Chem. Lett. 1975, 1201 et seq. and Bull. Chem. Soc. Japan, 51: 2077 et seq. (1978)] and workers from Rhône-Poulenc developed new routes to carotenoids and vitamin A (see DOS 2,701,489 and A.E.C. Société de Chimie Organique et Biologique No. 7824350).

Silylated vinylketene acetals [of the type $CH_2=CH-CH=C-(Oalkyl)(OSi(CH_3)_3)$] can also react with acetals in a manner analogous to the aforementioned trimethylsily-loxydienes [see Tetr. Lett., 20: 3209 et seq. (1979) and Chimia, 34: 265 et seq. (1980)]. As evident from, among others, Tetr. Lett., 22: 2833 et seq. (1981), ibid. 26: 397 et seq. (1985), DOS 3,244,273 and U.S. Pat. No. 4,937,308, the known reactions always formed not readily separable mixtures of the two possible γ- and α-coupling products ["γ-products"... $CH(Oalkyl^1)-CH_2-CH=CH-COOalkyl^2$; "α-products" ... $CH(Oalkyl^1)-C(CH_3)(CH=CH_2)-COOalkyl^2$], rendering this reaction—at best marginally usable for synthetic purposes in the carotenoid field. This reaction would be interesting and useful only if complete γ-selectivity could be achieved, for example for the synthesis of polyenes, namely apoesters, crocetin esters etc.; because by elimination of the alcohol alkyl[1]OH from the γ-product it is possible to form, if desired, a further (conjugated) double bond with the formation of the product ... $CH=CH-CH=CH-COOalkyl^2$. Thus, such polyenes could be produced without employing the Wittig or Horner reaction hitherto used for this purpose.

SUMMARY OF THE INVENTION

The present invention provides a process for manufacturing a compound of formula:

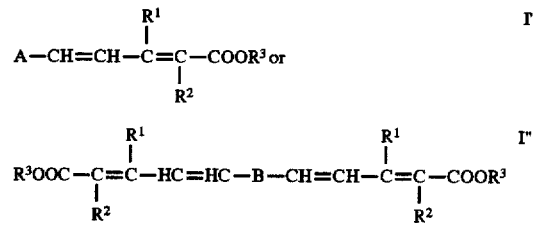

wherein

A is a monovalent conjugated polyene group or a methyl-substituted, monovalent conjugated polyene group, B is a bivalent conjugated polyene group or a methyl-substituted, bivalent conjugated polyene group, $R^1$ and $R^2$ each independently is hydrogen or methyl, and $R^3$ is hydrogen or $C_{1-6}$-alkyl, with the $-CH=CH-C(R^1)=C(R^2)-COOR^3$ group(s) in each case being situated in the terminal position(s) of the conjugated chain of group A or B.

This process comprises reacting a compound of formula:

or

wherein

A and B are as above, with the $-CH(OR^4)_2$ group(s) being situated in the terminal position(s) of the conjugated chain of group A or B, and $R^4$ is $C_{1-6}$-alkyl, with a compound of formula:

wherein $R^1$ and $R^2$ are as above, and $R^5$ is $C_{1-6}$-alkyl and $R^6$ is $C_{1-6}$-alkyl or tri($C_{1-6}$-alkyl)silyl, or $R^5$ and $R^6$ both are tri($C_{1-6}$-alkyl)silyl, or $R^5$ and $R^6$ together form 1,2-ethylene or 1,3-trimethylene, in the presence of a Lewis acid, and where a compound of formula III in which $R^5$ and $R^6$ both are $C_{1-6}$-alkyl or both are tri($C_{1-6}$-alkyl)silyl or together form 1,2-ethylene or 1,3-trimethylene is used, subsequently hydrolyzing the compound formed, so as to form in all cases a compound of the formula:

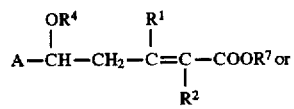

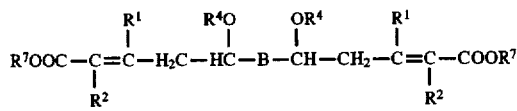

wherein

A, B, $R^1$, $R^2$ and $R^4$ are as above, with the —CH($R^4$)—CH$_2$—C($R^1$)=C($R^2$)COOR$^7$ group(s) being situated in the terminal position(s) of the conjugated chain of group A or B, and $R^7$ is $C_{1-6}$-alkyl, hydrogen, 2-hydroxyethyl or 3-hydroxy-n-propyl.

The $R^4$OH group is then cleaved from the compound of formula IV' or IV" under strong basic conditions, and where there is a difference between groups —COOR$^7$ and —COOR$^3$, the group —COOR$^7$ is converted to group —COOR$^3$.

Unique compounds provided by the present invention include compounds of the formula:

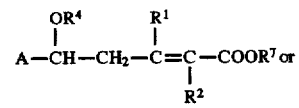

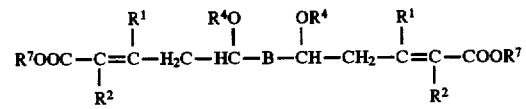

wherein

A is a monovalent conjugated polyene group or a methyl-substituted, monovalent conjugated polyene group, B is a bivalent conjugated polyene group or a methyl-substituted, bivalent conjugated polyene group, $R^1$ and $R^2$ each independently is hydrogen or methyl, $R^4$ is $C_{1-6}$-alkyl, and $R^7$ is $C_{1-6}$-alkyl, hydrogen, 2-hydroxyethyl or 3-hydroxy-n-propyl, with the —CH(OR$^4$)—CH$_2$—C($R^1$)=C($R^2$)—COOR$^7$ group(s) in each case being situated in the terminal position(s) of the conjugated chain of group A or B.

Another unique series of compounds include compounds of the formula:

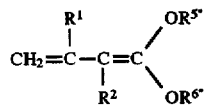

wherein $R^1$ and $R^2$ each independently is hydrogen or methyl and $R^{5''}$ and $R^{6''}$ each independently is $C_{1-6}$-alkyl, with the exception of 1,1-dimethoxy-1,3-butadiene and 1,1-diethoxy-3-methyl-1,3-butadiene.

Further unique compounds include compounds of the formula:

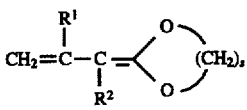

wherein $R^1$ and $R^2$ each independently is hydrogen or methyl, and s is 2 or 3, with the exception of 2-allylidene-[1,3]dioxolane, 2-(1-methyl-allylidene)-[1,3]dioxolane and 2-(2-methyl-allylidene)-[1,3]-dioxolane.

DETAILED DESCRIPTION OF THE INVENTION

The present invention will now be described in terms of its preferred embodiments. These embodiments are set forth to aid in understanding the invention, but are not to be construed as limiting.

An object of the present invention is to manufacture, starting from polyene (di)acetals and vinylketene acetals or silylated analogues thereof, correspondingly chain-lengthened polyene (di)esters or acids while avoiding as far as possible the aforementioned disadvantages of the state of the art and replacing the Wittig or Horner reaction hitherto used for this purpose.

This object is achieved in accordance with the invention by reacting a polyene (di)O,O-dialkyl acetal with a vinyl-O,O-dialkyl- or O,O-alkylene-ketene acetal or an O-mono- or O,O-disilylated analogue thereof in the presence of a Lewis acid to give the correspondingly chain-lengthened (bis)δ-alkoxy-γ,δ-saturated polyene ester or the corresponding (di)acid and subsequently eliminating the δ-positioned alkanol from the thus-formed (di)ester or from the corresponding (di)acid under basic conditions in order to obtain the desired (conjugated) polyene (di)ester or the corresponding (di)acid. Not only is the reaction of the vinyl-O,O-dialkyl- or vinyl-O,O-alkylene-ketene acetal or of the O-mono- or O,O-disilylated analogue with the polyene O,O-dialkyl acetal novel, but surprisingly it takes place (so far as can be seen) with exclusive attack at the γ-position of the vinylketene acetal derivative. By the subsequent base-induced elimination of the alkanol a (conjugated) C—C double bond is formed without requiring a phosphorus-containing or silicon-containing reagent, which is in contrast to the methodology hitherto usually used in this field.

Accordingly, the present invention is concerned with a process for the manufacture of a polyene ester or a polyene acid of the formula

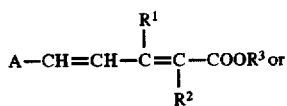

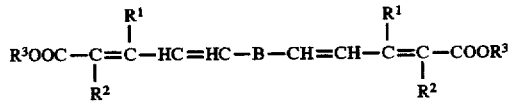

wherein

A signifies an optionally methyl-substituted, monovalent conjugated polyene group, B signifies an optionally methyl-substituted, bivalent conjugated polyene group, $R^1$ and $R^2$ each signify hydrogen or methyl and $R^3$ signifies hydrogen or $C_{1-6}$-alkyl, with the —CH=CH—C($R^1$)=C($R^2$)—COOR$^3$ group(s) in each case being situated in the terminal position(s) of the conjugated chain of group A or B, which process comprises reacting a polyene (di)O,O-dialkyl acetal of the formula $$A\text{—}CH(OR^4)_2 \quad \text{II'}$$

or $$(R^4O)_2HC\text{—}B\text{—}CH(OR^4)_2 \quad \text{II''}$$

wherein

A and B have the significances given above, with in this case the —$CH(OR^4)_2$ group(s) being situated in the terminal position(s) of the conjugated chain of group A or B and $R^4$ signifies $C_{1-6}$-alkyl, with a vinylketene acetal or analogue thereof of the formula

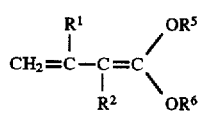

wherein $R^1$ and $R^2$ have the significances given above and $R^5$ signifies $C_{1-6}$-alkyl and $R^6$ signifies $C_{1-6}$-alkyl or tri($C_{1-6}$-alkyl)silyl or $R^5$ and $R^6$ both signify tri($C_{1-6}$-alkyl)silyl or $R^5$ and $R^6$ together form 1,2-ethylene or 1,3-trimethylene, in the presence of a Lewis acid, hydrolyzing the reaction mixture where a vinylketene acetal of formula III in which $R^5$ and $R^6$ both signify $C_{1-6}$-alkyl or both signify tri($C_{1-}$ 6-alkyl)silyl or together form 1,2-ethylene or 1,3-trimethylene is used, subsequently (in all cases) cleaving off the alcohol $R^4OH$ under strong basic conditions from the thus-produced compound of the formula

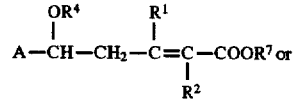

-continued

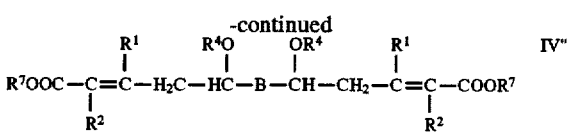

wherein

A, B, $R^1$, $R^2$ and $R^4$ have the significances given above, with in this case the —$CH(OR^4)$—$CH_2$—$C(R^1)$=C($R^2$)$COOR^7$ group(s) being situated in the terminal position(s) of the conjugated chain of group A or B, and $R^7$ signifies $C_{1-6}$-alkyl, hydrogen, 2-hydroxyethyl or 3-hydroxy-n-propyl, and, where there is a difference between group(s) —$COOR^7$ and —$COOR^3$, converting the former into the latter.

The process in accordance with the invention can in principle be used in the case of all of the aforementioned polyene O,O-dialkyl acetals of formula II' or polyene di(O, O-dialkyl acetals) of formula II'' which have the acetal group —$CH(OR^4)_2$ at the end or at both ends of the polyene chain. Among such educts there are to be found, inter alia, the following sub-classes [with the abbreviated form of presentation which is usual in carotenoid chemistry (using simple lines) being used for the structural formulas]:

Alicyclic-aliphatic polyene O,O-dialkyl acetals, which mainly belong to the carotenoid field [as acetals of asymmetric carotenoid aldehydes having a six-membered (cyclohexene) ring], of the formula

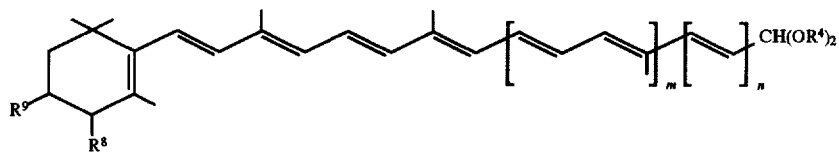

wherein $R^4$ has the significance given above and $R^8$ and $R^9$ each independently signify hydrogen, an optionally protected hydroxy group or an optionally protected oxo group, m signifies 0, 1, 2, 3 or 4 and n signifies 0 or 1, which, after carrying out the multistage process in accordance with the invention, are converted into the corresponding alicyclic-aliphatic polyene esters or acids of the formula

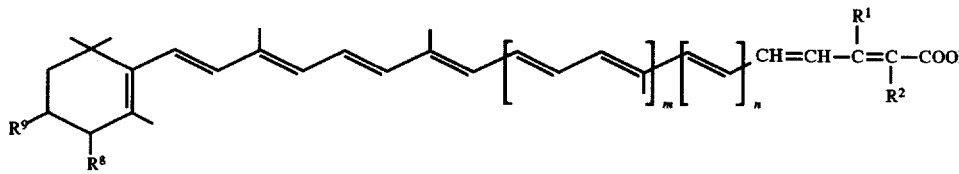

aliphatic polyene O,O-dialkyl acetals, which likewise mainly belong to the carotenoid field (as acetals of open-chain asymmetric carotenoid aldehydes), of the formula

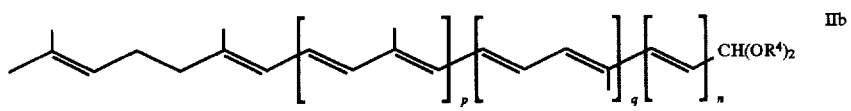

wherein
- $R^4$ has the significance given above and
- p signifies 0, 1 or 2,
- q signifies 0, 1, 2 or 3 and
- n signifies 0 or 1, which, after carrying out the multistage process in accordance with the invention, are converted into the corresponding aliphatic polyene esters or acids of the formula

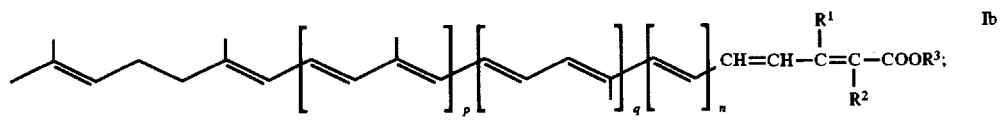

aliphatic polyene di(O,O-dialkyl acetals), which likewise mainly belong to the carotenoid field (as acetals of symmetrical carotenoid dialdehydes), of the formula

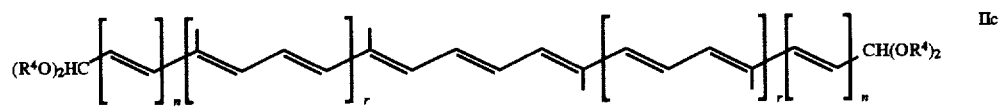

wherein
- $R^4$ has the significance given above and
- r signifies 0, 1 or 2 and
- n signifies 0 or 1, which, after carrying out the multistage process in accordance with the invention, are converted into the corresponding aliphatic polyene diesters or diacids of the formula

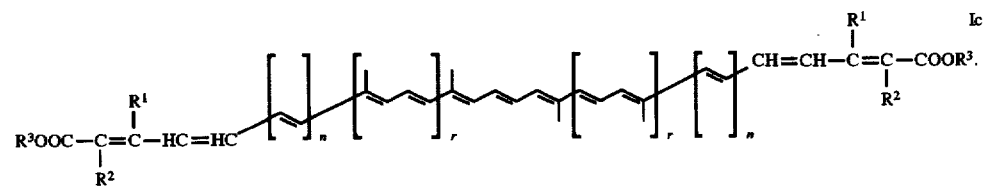

The educts of formulas IIa, IIb and IIc can be embraced by formula II:

wherein

R signifies a group (a), (b) or (c)

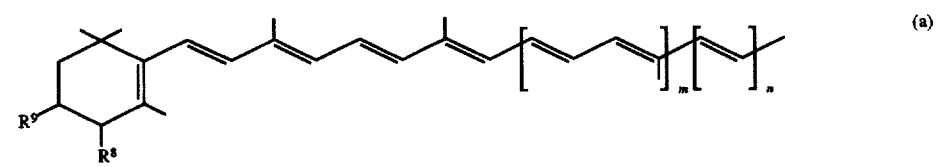

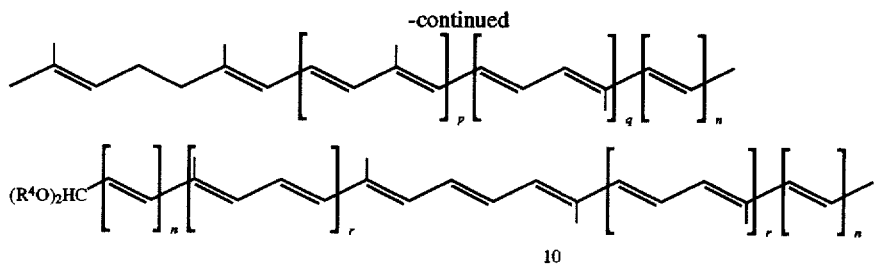

and

R$^4$, R$^8$, R$^9$, m, n, p, q and r have the significances given above.

After carrying out the multistage process in accordance with the invention the educt of formula II is converted into the corresponding product of formula I:

wherein R' has the significance of R given above, with the dialkoxymethyl group (R$^4$O)$_2$HC— being replaced by the group R$^3$OOC—C(R$^2$)=C(R$^1$)—HC=HC— where R' signifies a group (c).

Formula I then embraces formulas Ia, Ib and Ic.

Where the product of formula I, especially of formula Ia, has one or two protected groups (R$^8$, R$^9$) on the cyclohexene ring, the protecting group(s) present can, if desired, be cleaved off, which represents a further aspect of the present invention.

In the scope of the present invention the term "C$_{1-6}$-alkyl" embraces straight-chain and branched groups such as, for example, methyl, ethyl and isobutyl. This applies to the C$_{1-6}$-alkyl group of a group containing this, e.g. tri(C$_{1-6}$-alkyl)silyl.

The term "protected hydroxy group" embraces usual protected hydroxy groups (especially those which are familiar from the carotenoid field), particularly etherified hydroxy groups and acyloxy groups. The "etherified hydroxy groups" are, for example, C$_{1-5}$-alkoxy groups, preferably methoxy and ethoxy; C$_{2-16}$-alkoxyalkoxy groups, preferably 1-methoxy-1-methylethoxy; arylalkoxy groups, preferably benzyloxy; tetrahydropyranyloxy; and tri(C$_{1-5}$-alkyl) silyloxy groups, preferably trimethylsilyloxy. The acyloxy groups embrace especially alkanoyloxy and aroyloxy groups with up to 8 carbon atoms such as, for example, formyloxy, acetoxy, propionyloxy and benzoyloxy.

The term "protected oxo group" also embraces usual protected oxo groups (especially those which are familiar from the carotenoid field). Acetalized oxo groups, especially those in which the term protected oxo stands for two C$_{1-5}$-alkoxy groups (e.g. two methoxy groups) or for a C$_{2-6}$-alkylenedioxy group (e.g. ethylenedioxy or 2,3-butylenedioxy) are preferred. Further, an oxo group can also be protected as an enol ether, primarily in the case of α-hydroxy-ketones (e.g. R$^8$ and R$^9$ signify hydroxy or oxo or vice versa), whereby the etherification of the enediol can preferably also be effected by the formation of a cyclic acetal or ketal (e.g. with acetone to the acetonide). The oxo group can also be protected, for example, as an imine.

The formulas of polyenes disclosed in the scope of the present invention embrace in each case isomeric forms, e.g. optically active and cis/trans or E/Z isomers, as well as mixtures thereof unless indicated to the contrary. The carbon atom carrying the residue R$^8$ or R$^9$ where R$^8$ or R$^9$ signifies an optionally protected hydroxy group (see formulas Ia and IIa) can be mentioned as an example of a chiral (optically active) centre. With respect to E/Z isomerism, then there are generally preferred the (all-E) isomers of the educts and of the products of the process in accordance with the invention.

The first process step of the process in accordance with the invention is conveniently carried out by reacting the polyene (di)O,O-dialkyl acetal of formula II' or II" with the vinylketene acetal (analogue) of formula III in an organic solvent at temperatures in the range of about –40° C. to about 100° C., preferably in the temperature range of about –20° C. to room temperature, and in the presence of a Lewis acid. Suitable organic solvents are, in general, all aprotic polar or non-polar solvents. Especially preferred among such solvents are lower aliphatic and cyclic hydrocarbons, e.g. n-pentane, n-hexane and cyclohexane; lower, halogenated aliphatic hydrocarbons, e.g. methylene chloride and chloroform; lower aliphatic and cyclic ethers, e.g. diethyl ether, tert.butyl methyl ether and tetrahydrofuran; lower aliphatic nitriles, e.g. acetonitrile; as well as aromatics, e.g. toluene. Examples of Lewis acids which can be used are zinc chloride, zinc bromide, titanium tetrachloride, lithium perchlorate, boron trifluoride etherate as well as iron(III) chloride; these are generally used in catalytic amounts, conveniently in an amount of between about 0.1 and 10 mol percent based on the amount of polyene (di)O,O-dialkyl acetal employed and preferably in a mol percent range of 1 to 3. Moreover, about 1.1 to about 1.6 equivalents, preferably about 1.3 to about 1.4 equivalents, of vinylketene acetal (analogue) are conveniently used per equivalent of polyene (di)O,O-dialkyl acetal. Furthermore, the reaction is conveniently effected at normal pressure, although generally the pressure is not critical.

Where a vinylketene acetal of formula III in which R$^5$ and R$^6$ both signify C$_{1-6}$-alkyl or together form 1,2-ethylene or 1,3-trimethylene is used, a compound of formula IV' or IV" is not produced after reacting the polyene (di)O,O-dialkyl acetal of formula II or II' with this vinylketene acetal, but instead there is produced an intermediate of the formula

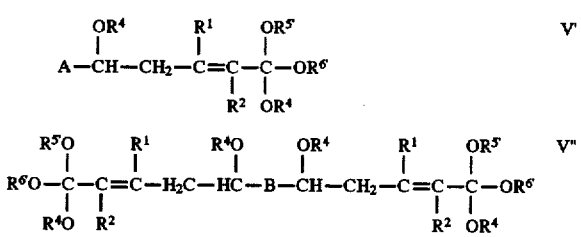

wherein

A, B, R$^1$, R$^2$ and R$^4$ have the significances given above and R$^5$ and R$^6$ both signify C$_{1-6}$-alkyl or together form 1,2-ethylene or 1,3-trimethylene.

Also when a vinylketene acetal of formula III in which R$^5$ and R$^6$ both signify tri(C$_{1-6}$-alkyl)silyl is used, a compound of formula IV' or IV" is not produced after reaction of the polyene (di)O,O-dialkyl acetal of formula II' or II" with this vinylketene acetal, but instead in this case there is produced an intermediate of the formula

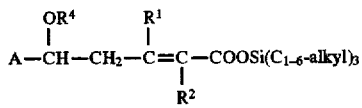   V'''

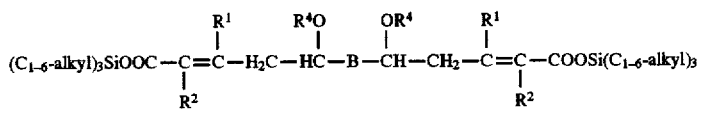   V'''' wherein A, B, R¹, R² and R⁴ have the significances given above.

If desired, the respective intermediate can be isolated from the reaction mixture and subsequently hydrolyzed to the corresponding compound of formula IV' or IV" [in which $R^7$ in each case signifies $C_{1-6}$-alkyl ($R^5$ and $R^6$ both signify $C_{1-6}$-alkyl), 2-hydroxyethyl or 3-hydroxy-n-propyl ($R^5$ and $R^6$ together form 1,2-ethylene or 1,3-trimethylene) or hydrogen (starting from the 1 5 intermediate of formula V''' or V"")]. However, it has been found to be convenient not to undertake such an isolation and subsequent hydrolysis, but to hydrolyze the intermediate in the reaction mixture immediately after completion of the reaction II/II"+ III→V'/V"/V'''/V"" in order in these cases to proceed to the compound of formula IV' or IV" (hereinafter abbreviated to IV'/IV"). Starting from an intermediate of formula V' or V" the hydrolysis can be suitable effected by adding to the reaction mixture an aqueous solution of a weak acid, preferably slightly diluted aqueous acetic acid, and subsequently stirring the mixture for a time, for example about 30 minutes to about 2 hours, conveniently in the temperature range of about 0° C. to room temperature. In the other case, i.e. starting from an intermediate of formula V''' or V"", the hydrolysis takes place much more readily, namely with water alone; the hydrolysis can even be effected in the course of the normal working-up, whereby water is mainly used as the purifying agent.

Depending on the vinylketene acetal (analogue) of formula III which is used there is obtained, after carrying out the first process step as well as any hydrolysis which may be required, as explained in more detail above, the corresponding product of formula IV'/IV", namely:

after using a vinylketene acetal (analogue) of formula III in which $R^5$ signifies $C_{1-6}$-alkyl and $R^6$ signifies $C_{1-6}$-alkyl or tri($C_{1-6}$-alkyl)silyl, a compound of formula IV'/IV" in which $R^7$ signifies $C_{1-6}$-alkyl (when $R^6$ signifies tri($C_{1-6}$-alkyl)silyl, this group is eliminated);

after using a vinylketene acetal analogue of formula III in which $R^5$ and $R^6$ both signify tri($C_{1-6}$-alkyl)silyl, a compound of formula IV'/IV" in which $R^7$ signifies hydrogen [both tri($C_{1-6}$-alkyl)silyl groups are eliminated and the product has one or two terminal 4-carboxy-1-($C_{1-6}$-alkoxy)-3-butenyl group(s) or corresponding 3- and/4-methyl substituted ($R^1$ and/or $R^2$=methyl) group(s) —CH(OR⁴)—CH₂—C(R¹)=C(R²)—COOH]; and after using a vinylketene acetal of formula III in which $R^5$ and $R^6$ together form 1,2-ethylene or 1,3-trimethylene, a compound of formula IV'/IV" in which $R^7$ signifies 2-hydroxyethyl or 3-hydroxy-n-propyl.

The respective product can be isolated from the reaction mixture and, if desired, purified in a manner known per se. Typically, the mixture is combined with water and the batch is extracted with a water-immiscible organic solvent such as, for example, with a lower alkane or dialkyl ether, e.g. n-hexane or tert.butyl methyl ether, and the organic phase is washed with water and/or saturated aqueous sodium chloride and/or sodium bicarbonate solution, dried and concentrated. The thus-isolated and at least to some extent washed crude product can then, if desired, be purified further, for example by column chromatography, e.g. using eluents such as n-hexane, ethyl acetate, toluene or mixtures thereof, or (re)crystallization, for example from an alcohol, e.g. methanol or ethanol. Alternatively, and often preferably, the crude product taken up, for example, in a lower alkanol can be reacted directly in the last process step (cleavage of the alcohol R⁴OH) of the present invention, i.e. in the sense of a "through process" II/II"+III→IV'/IV"→I'/I".

The last process step is conveniently carried out by subjecting the compound of formula IV'/IV" dissolved in a suitable organic solvent to strongly basic conditions, i.e. reacting it in the presence of a base with cleavage of the alcohol R⁴OH to the corresponding polyene ester or acid. Suitable organic solvents are, in general, polar or non-polar solvents such as, for example, alcohols, aliphatic or cyclic ethers, e.g. diethyl ether and tetrahydrofuran, and aliphatic esters, e.g. ethyl acetate; or, respectively, aromatics, e.g. toluene, aliphatic hydrocarbons, e.g. n-hexane, and lower halogenated aliphatic hydrocarbons, e.g. methylene chloride, chloroform and carbon tetrachloride; or also mixtures of an alcohol with another solvent mentioned here. Where an alcohol of the formula R³OH in which $R^3$ is different from $R^7$ (as $C_{1-6}$-alkyl, 2-hydroxyethyl or 3-hydroxy-n-propyl) in the compound of formula IV'/IV" is used as the solvent, the final product of formula I' or I" has the respective ester group —COOR³ as a result of the excess amount of alcohol R³OH vis-à-vis this intermediate: in this (quite simple) manner, i.e. by transesterification, the ester group —COOR⁷ is converted into the ester group —COOR³ which is different therefrom. Otherwise, a separate treatment, i.e. trans-esterification of the isolated product which has the ester group —COOR⁷ is carried out in a manner known per se in order to convert the group —COOR⁷ into the desired ester group —COOR³ which is different therefrom.

The base which is used can be inorganic or organic, there being suitable in general strong bases such as, for example, alkali metal alcoholates, especially sodium methylate, sodium ethylate, potassium methylate, potassium ethylate and potassium tert.butylate, as well as alkali metal hydrides, especially sodium hydride.

Conveniently, at least one equivalent of base, preferably about 1.5 to about 2 equivalents, is used per equivalent of the compound of formula IV' or IV". The reaction is suitably effected in a temperature range of about 0° C. to about 100° C., preferably at temperatures of about room temperature to about 50° C. Moreover, the reaction is conveniently effected at normal pressure, although in general the pressure is not critical.

It has been found to be especially advantageous to carry out the last process step using a sodium alkoxide as the base and the corresponding alkanol as the solvent at temperatures between room temperature and the reflux temperature of the respective reaction mixture, preferably in a temperature range of about 40° C. to about 60° C. Conveniently, either a solution of the sodium alkoxide in the alcohol is prepared in advance or this solution is prepared freshly from metallic sodium and the alkanol. The bringing together of the alkanolic solution of the sodium alkoxide with the solution of the compound of formula IV'/IV" in the (same) alkanol, preferably likewise previously prepared, can be effected in any sequence and preferably at room temperature. Then, the reaction mixture is subsequently stirred for several hours and the reaction has normally finished at the the latest after 24 hours.

Irrespective of the chosen procedure for the last process step, the product can be isolated from the reaction mixture and purified in a manner known per se. The respective working-up normally comprises neutralization of the remaining base by addition of an organic or inorganic acid such as, for example, a carboxylic acid, e.g. acetic acid, or an aqueous mineral acid, e.g. dilute sulphuric acid.

In the particular embodiment of the procedure described above using a sodium alkoxide as the base, after completion of the reaction the mixture is conveniently cooled to room temperature or even to about 0° C. and thereafter preferably neutralized with aqueous acetic acid, which normally leads to (possibly further) crystallization of the product of formula I' or I". The crystallization can also be expedited by further cooling. After its isolation, suitably by filtration, the product can be washed, for example with water and/or aqueous alcohol, and finally dried, optionally under reduced pressure. If desired, further methods such as, for example, column chromatography and recrystallization can be employed in order to provide an even purer product.

The cleavage of the alcohol $R^4OH$ from the compound of formula IV'/IV" can also be effected under acidic conditions in order to serve as an alternative to the last process step of the process in accordance with the invention which is effected under strongly basic conditions. After pertinent experiments to bring about this cleavage using catalytic amounts of a strong acid, e.g. p-toluenesulphonic acid, it has been established that the cleavage actually proceeds relatively readily. For example, when using 12'-methoxy-11', 12'-dihydro-8'-apo-β-carotenoic acid ethyl ester with a catalytic amount of p-toluenesulphonic acid in methylene chloride at about 0° C. the cleavage of methanol was effected after about 30 minutes and gave crude 8'-apo-β-carotenoic acid ethyl ester in almost quantitative yield by weight. According to HPLC the crude product consisted to the extent of about 71.5% of the. (all E) isomer and of several additional [presumably (Z)] isomers. The absolute content of the crude product was, however, only about 37.5% according to HPLC. Possibly, a partial polymerization of the polyene system takes place under such strongly acidic conditions. Further attempts to optimise this acid-catalyzed cleavage brought no improved results. Surprisingly, it was established that the cleavage effected under basic conditions leads almost exclusively to the desired (all E) isomer, with almost no (Z) isomers and further undesired isomers being formed.

Depending on the compound of formula IV' or IV" and solvent (alcoholic or other solvent) used there is obtained after carrying out the last process step the product of formula I' or I" (abbreviated hereinafter to I'/I"), respectively, appropriate to the residue $R^3$. Where the solvent is not an alcohol (so that no trans-esterification can then take place), there is obtained:

after using a compound of formula IV'/IV" in which $R^7$ signifies $C_{1-6}$-alkyl, a polyene ester/diester of formula I'/I" in which $R^3$ signifies the corresponding $C_{1-6}$-alkyl;

after using a compound of formula IV'/IV" in which $R^7$ signifies hydrogen, a polyene acid/diacid of formula I'/I" in which $R^3$ signifies hydrogen; and after using a compound of formula IV'/IV" in which $R^7$ signifies 2-hydroxyethyl or 3-hydroxy-n-propyl, a polyene ester/diester of formula I'/I" in which $R^3$ does not have the significance hitherto given, but signifies 2-hydroxyethyl or 3-hydroxy-n-propyl.

In each of the above three cases the residue $R^7$ remains unaltered in the course of the last process step.

On the other hand, where an alcohol, especially a $C_{1-6}$-alkanol, is used as the solvent and when the three types of compounds IV'/IV" are used, a trans-esterification takes place in two cases (in the first and third case) as already indicated above. In this manner there is formed in each case a polyene ester of formula I'/I" in which $R^3$ corresponds to the respective alkyl residue of the alkanol: the group —$COOR^7$ in the compound IV'/IV" is thus converted without particular measures into the group —$COOR^3$ which is different therefrom, unless the alcoholic solvent corresponds to the alcohol $R^7OH$. The use of the respective alkanol $R^3OH$ is preferred for this reason and also because the product of formula I, which is difficultly soluble in the alcohol, crystallizes out from the solution already during the reaction.

If desired, protecting groups ($R^8$ and/or $R^9$ as a protected hydroxy or oxo group) which may be present in the product of formula I' or I" obtained can be cleaved off according to methods known per se, e.g. by hydrolysis with acid or base.

While some of the educts of the process in accordance with the invention are known, other precursors, which are in part known, can be produced according to methods known per se.

Thus, for example, the polyene O,O-dialkyl acetals of formula II' and the polyene di(O,O-dialkyl acetals) of formula II" can be produced very readily in a generally known manner by reacting the polyene monoaldehyde of the formula A—CHO or polyene dialdehyde of the formula OHC—B—CHO with the respective trialkyl orthoformate, especially in the corresponding $C_{1-6}$-alkanol, e.g. methanol for the O,O-dimethyl acetal, and in the presence of a catalytic amount of an organic acid or a Lewis acid, e.g. p-toluenesulphonic acid or zinc chloride (see, for example, Organikum, Organisch-chemisches Grundpraktikum, 6th edition, p. 377 et seq. (1963)]. The reaction takes place in suspension; i.e. the respective polyene monoaldehyde or dialdehyde is suspended in the alkanol and then conveniently about two or four mol equivalents, respectively, of the trialkyl orthoformate are added to the suspension, followed by a trace of acidic catalyst, e.g. p-toluenesulphonic acid. Thereby, the monoaldehyde or dialdehyde dissolves slowly and the polyene O,O-dialkyl acetal or di(O,O-dialkyl acetal) of formula II'/II" simultaneously crystallizes out slowly. The reaction is conveniently carried out in a temperature range of about 0° C. to about 40° C., and as a rule takes about 2 to about 4 hours. As further literature sources which illustrate the generally known acetalization method reference is made to European Patent Publication Nos. 0 252 389 and 0 391 033 as well as to J. Mol. Cat., 79: 117 et seq. (1993).

The polyene monoaldehydes A—CHO and dialdehydes OHC—B—CHO in turn are either known, especially from the technical literature concerning carotenoids, or—where novel—can be produced according to methods known per se. Thus, for example, the reaction of various $C_{15}$-Wittig salts with 2,7-dimethyl-2,4,6-octatrienedial (the so-called "$C_{10}$-dialdehyde") to give the corresponding monoaldehydes, the reaction of various $C_5$-Wittig aldehydes with long-chain polyene aldehydes likewise to give such monoaldehydes as well as the two-fold reaction of the $C_{10}$-dialdehyde with $C_5$- or $C_{10}$-Wittig aldehydes to give various dialdehydes are known from this literature. The textbook "Carotenoids" (O. Isler, published by Birkhäuser, Basel and Stuttgart, 1971), especially chapters VI and XII thereof and the further literature mentioned therein, provides much useful information relating to the production and the occurrence of the known monoaldehydes and dialdehydes. Where educts which have protected hydroxy, oxo or formyl groups are used, then such "protected" educts can be produced, for example, directly from the corresponding unprotected educts according to methods known per se.

The vinylketene acetals or analogues thereof of formula III are in part known compounds; the majority of these educts are, however, novel.

Certain compounds of formula III in which $R^5$ and $R^6$ each independently signify $C_{1-6}$-alkyl are known: these are especially 1,1-dimethoxy-1,3-butadiene and 1,1-diethoxy-3-methyl-1,3-butadiene (formula III in which $R^1$ and $R^2$ both signify hydrogen and $R^5$ and $R^6$ both signify methyl and, respectively, $R^1$ signifies methyl, $R^2$ signifies hydrogen and $R^5$ and $R^6$ both signify ethyl). The remaining compounds of this sub-class are considered to be novel. All of these compounds can be produced in accordance with the following Reaction Scheme starting from a nitrile of formula VI which is known or which can be produced according to methods known per se:

alkanol $R^{5''}OH$, to give the orthoester of formula VIII is conveniently effected in an aprotic solvent, e.g. one of the aforementioned solvents, and at temperatures in the range of about 0° C. to about 60° C., preferably at room temperature.

One equivalent of alkanol $R^{6''}OH$ can be eliminated from the orthoester of formula VIII using sodium amide in liquid ammonia as the base or solvent, with the desired vinylketene acetal of formula IIIa being obtained very easily. Other base/solvent combinations can be used for this purpose, especially an alkali metal amide (generally) or an alkali metal alkyl, e.g. butyllithium, in each instance in a polar or apolar aprotic solvent such as, for example, a lower aliphatic hydrocarbon, e.g. n-hexane, a lower aliphatic ether, e.g. diethyl ether, or an aromatic, e.g. benzene or toluene.

Of those vinylketene acetal analogues of formula III in which $R^5$ signifies $C_{1-6}$-alkyl and $R^6$ signifies tri($C_{1-6}$-alkyl)silyl, at least 1-trimethylsilyloxy-1-ethoxy-2-methyl-1,3-butadiene (formula III in which $R^1$ signifies hydrogen, $R^2$ signifies methyl, $R^5$ signifies ethyl and $R^6$ signifies trimethylsilyl) is known [see, inter alia, Tetr. Lett., 20: 3209 et seq. (1979), Chimia, 34: 265 et seq. (1980) and Tetr. Lett., 26: 397 et seq. (1985)]. Those analogues which are novel can be produced, for example, from the corresponding alkyl 3-butenoate by reaction with lithium diisopropylamide and the corresponding trialkylsilyl chloride at low temperatures, e.g. about −70° C. [see especially Tetrahedron, 40: 3455 et seq. (1984)]. The aforementioned alkyl 3-butenoates (starting materials) are, in turn, known or can be produced according to methods known per se; ethyl 2-methyl-3-butenoate can be produced, for example, by ethanolysis of 2-methyl-3-butenenitrile (formula VI in which $R^1$ signifies hydrogen and $R^2$ signifies methyl), a byproduct in the synthesis of adiponitrile (Pinner reaction; see German Offenlegungsschrift 3,244,273, as well as U.S. Pat. No. 4,937,308).

Reaction Scheme 1

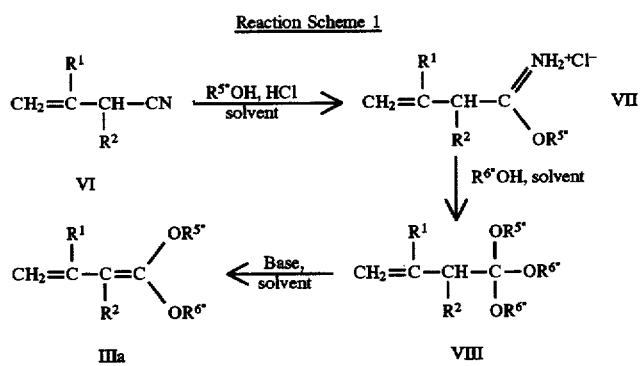

wherein $R^1$ and $R^2$ have the significances given above and $R^{5''}$ and $R^{6''}$ each independently signify $C_{1-6}$-alkyl.

The reaction of the nitrile of formula VI with the alkanol $R^{5''}OH$ in the presence of gaseous hydrogen chloride gives the corresponding iminoalkyl ester of formula VII, which in most cases is present in crystalline form. An aprotic solvent, especially a lower aliphatic hydrocarbon, e.g. n-pentane or n-hexane; a lower halogenated aliphatic hydrocarbon, e.g. methylene chloride or chloroform; or a aromatic, e.g. benzene or toluene, is suitably used as the solvent. Both the alkanol and the hydrogen chloride are conveniently used in slight excess, namely up to about 50%; preferably up to about 10 and, respectively, 20% (equivalents of alkanol and hydrogen chloride, respectively, relative to equivalents of nitrile). The reaction is suitably effected in a temperature range of about −20° C. to about +60° C., preferably in a temperature range of about 0° C. to room temperature.

The further reaction of the iminoalkyl ester with the alkanol $R^{6''}OH$, which may if desired be different from the A further sub-class of vinylketene acetals or analogues thereof of formula III likewise includes known compounds, e.g. 1,1-di(trimethylsilyloxy)-2-methyl-1,3-butadiene [formula III in which $R^1$ signifies hydrogen, $R^2$ signifies methyl and $R^5$ and $R^6$ both signify trimethylsilyl; see J.A.C.S., 110: 5841 et seq. (1988)]. In total, this sub-class consists of vinylketene acetal analogues of formula III in which $R^5$ and $R^6$ both signify tri($C_{1-6}$-alkyl)silyl. The aforementioned known analogue can be produced, for example, starting from 2-methyl-3-butenoic acid trimethylsilyl ester by deprotonization using lithium diisopropylamide at about −75° C. and subsequent reaction with trimethylsilyl chloride in accordance with the conditions given in J. Organomet. Chem., 338: 149 et seq. (1988). The remaining analogues of this type can be produced in a similar manner.

The remaining vinylketene acetals of formula III are novel compounds with three exceptions. The exceptions are 2-alkylidene-[1,3]dioxolane, 2-(1-methyl-allylidene)-[1,3]

dioxolane and 2-(2-methyl-allylidene)-[1,3]dioxolane (formula III in which $R^1$ and $R^2$ both signify hydrogen, $R^1$ signifies hydrogen and $R^2$ signifies methyl or $R^1$ signifies methyl and $R^2$ signifies hydrogen, respectively, and $R^5$ and $R^6$ in each case together form 1,2-ethylene). The synthesis of the second-named compound is published in Tetrahedron, 50: 5109–5118 (1994); the acetal was produced in mg amounts starting from tiglic acid, but was not isolated and was only detected by $^1$H-NMR spectroscopy (capillary tube). Other relevant literature sources concerning the three known vinylketene acetals are J. Chem. Soc., Perkin Trans., 1(5): 1582–4 (1981) and Macromolecules, 28(12): 4319–4325 (1995).

In general, the vinylketene acetals of this particular subclass, i.e. of formula III in which $R^5$ and $R^6$ together form 1,2-ethylene or 1,3-trimethylene, can be produced in accordance with the following Reaction Scheme (as in the case of Reaction Scheme 1 starting from the nitrile of formula VI):

These novel compounds of formulas IV' and IV" include:

15-Methoxy-15,15'-dihydro-12'-β-carotenoic acid ethyl ester, 15-methoxy-15,15'-dihydro-12'-apocarotenoic acid methyl ester, 12'-methoxy-11',12'-dihydro-8'-apo-β-carotenoic acid ethyl ester, 12'-methoxy-11',12'-dihydro-8'-apo-β-carotenoic acid methyl ester, 12'-methoxy-11',12'-dihydro-8'-apo-β-carotenoic acid 2-hydroxyethyl ester, 8'-methoxy-7',8'-dihydro-4'-apo-β-carotenoic acid ethyl ester, 8'-methoxy-7',8'-dihydro-4'-apo-β-carotenoic acid methyl ester, 4'-methoxy-β,ψ-caroten-16'-oic acid ethyl ester, 4'-methoxy-β,ψ-caroten-16'-oic acid methyl ester,

Reaction Scheme 2

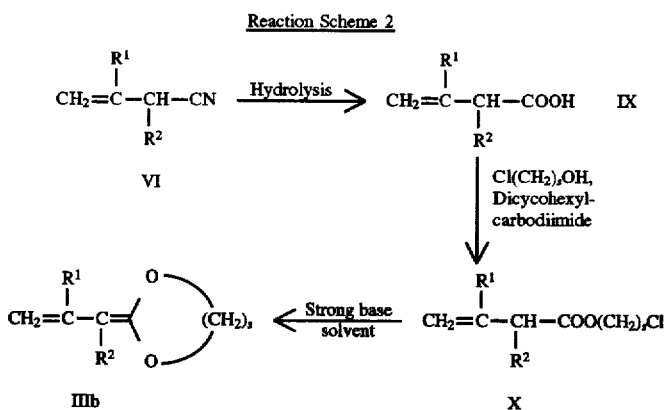

wherein $R^1$ and $R^2$ have the significances given above and s signifies 2 or 3.

The hydrolysis of the nitrile of formula VI to the corresponding carboxylic acid of formula IX and the subsequent esterification of this carboxylic acid to the ester of formula X can in each case be carried out in a manner known per se [see, for example, Organikum, Organisch-chemisches Grundpraktikum, 6th edition, p. 411 et seq. (1967) and, respectively, J. March, Advanced Organic Chemistry, 3rd edition, p. 349 et seq. (1989)]. Then, the cyclization of the ester to the desired [1,3]dioxolane or [1,3]dioxane can be conveniently effected in an aprotic polar or non-polar solvent, especially a lower aliphatic hydrocarbon, e.g. n-hexane, a lower aliphatic ether, e.g. diethyl ether, or an aromatic, e.g. toluene, in the presence of a strong base, especially an alkali metal alkyl, e.g. methyllithium or butyllithium, an alkali metal hydride, e.g. sodium hydride or potassium hydride, or an alkali metal amide, e.g. lithium amide, sodium amide or potassium amide or lithium diisopropylamide, at temperatures in the range of about –70° C. to about +100° C., preferably in a temperature range of about –30° C. to about 0° C.

In the production of the vinylketene acetals or analogues thereof described above, the product or an intermediate can in each case be isolated and purified in a manner known per se.

The intermediates of the process in accordance with the invention, i.e. the compounds of formulas IV' and IV", are novel compounds and represent a further aspect of the present invention.

12'-methoxy-11,12'-dihydro-8'-apo-β-caroten-8'-oic acid, 11,12,11',12'-tetrahydro-12,12'-dimethoxy-8,8'-diapocarotene-8,8'-dioic acid ethyl ester, 11,12,11',12'-tetrahydro-12,12'-dimethoxy-8,8'-diapocarotene-8,8'-dioic acid methyl ester, 7,8,7',8'-tetrahydro-8,8'-dimethoxy-4,4'-diapocarotene-4,4'-dioic acid ethyl ester and 7,8,7',8'-tetrahydro-8,8'-dimethoxy-4,4'-diapocarotene-4,4'-dioic acid methyl ester.

Certain of the novel starting materials (vinylketene acetals and analogues thereof) of formula III used for the production of the above intermediates of formulas IV' and IV" and ultimately of the polyene esters and acids of formulas I' and I" represent a further aspect of the present invention. These novel starting materials in accordance with the invention are the compounds of the previously given formula IIIa with the exception of 1,1-dimethoxy-1,3-butadiene and 1,1-diethoxy-3-methyl-1,3-butadiene and those of the also previously given formula IIIb with the exception of 2-allylidene-[1,3]dioxolane, 2-(1-methyl-allylidene)-[1,3] dioxolane and 2-(2-methyl-allylidene)-[1,3]dioxolane. These novel compounds include:

1,1-Dimethoxy-2-methyl-1,3-butadiene, 1,1-dimethoxy-3-methyl-1,3-butadiene, 1,1-diethoxy-1,3-butadiene, 1,1-diethoxy-2-methyl-1,3-butadiene, 2-(1,2-dimethyl-allylidene)-[1,3]dioxolane and 2-(1-methyl-allylidene)-[1,3]dioxane.

The final products of the process in accordance with the invention, i.e. the polyene esters and acids of formulas I' and I", belong for the most part to the carotenoid field and can be used appropriately, for example as colorants or pigments for foodstuffs, egg yolk, the integuments (especially skin, legs and beak) and/or the subcutaneous fat of poultry, the flesh and/or the integuments (especially skin, scales and shell) of fish and crustaceans etc. This use can be effected according to methods known per se, as described, for example, in European Patent Publication No. 0 630 578.

The use of the novel final products represents a further aspect of the present invention.

The invention is illustrated on the basis of the following Examples.

A. Production of Polyene (di)O,O-dialkyl Acetals
(Compounds of Formulas II' and II")

EXAMPLE 1

15-Apo-β-Carotenal Dimethyl Acetal (Vitamin A Aldehyde Dimethyl Acetal)

2.84 g (10 mmol) of vitamin A aldehyde (>99% pure) were placed in 30 ml of methanol and 11 ml (100 mmol, 10 eq.) of trimethyl orthoformate in a 100 ml four-necked sulphonation flask equipped with a magnetic stirrer, argon gasification and a thermometer. 40 mg (0.3 mmol, 3 mol %) of anhydrous zinc chloride were added thereto at 0° C. and the mixture was stirred at 0° C. for 3½ hours. Then it was cooled to −40° C. within one hour and filtered, and the solid was washed with a small amount of cold (at about −10° C.) methanol and finally dried. This gave 2.5 g (75% yield) of (all-E)-vitamin A aldehyde dimethyl acetal with m.p. 53°–56° C.; content according to HPLC: 98.4%.

For analysis, a sample was recrystallized from methanol. This sample showed the following physical and analytical data: m.p. 53°–55° C.; content according to HPLC: 99.7%; UV (n-hexane): 324 nm (log $\epsilon$=4.70; E=1520).

Microanalysis: Calc.: C 79.95% H 10.37% Found: C 79.66% H 10.50%

EXAMPLE 2

12'-Apo-β-Carotenal Dimethyl Acetal 50 g (0.14 mol) of 12'-apo-β-carotenal and 31 ml (30.1 g, 0.28 mol) of freshly distilled trimethyl orthoformate in 500 ml of methanol were placed in a 1.5 l four-necked sulphonation flask equipped with a mechanical stirrer, argon gasification and a thermometer. A solution of 16 mg of p-toluenesulphonic acid monohydrate in 4 ml of methanol was then added at room temperature to the resulting suspension. Thereby, the red crystals dissolved for the most part within 20 minutes; subsequently an orange precipitate began to form. After stirring at room temperature for 2 hours the mixture was cooled to about +5° C., 0.5 ml of triethylamine was added, the mixture was stirred at 0° C. for 15 minutes, suction filtered (pressure suction filter, under argon), and the solid washed with a small amount of cold (−10° C.) methanol and dried at room temperature for about 16 hours under reduced pressure (water-jet vacuum). This gave 52.3 g (90.5% yield) of 12'-apo-β-carotenal dimethyl acetal as an orange powder with m.p. 77°–78° C.; content according to HPLC: 97.5% (very acid-labile); UV (n-hexane): 393 nm (log $\epsilon$=4.91; E=2045), 376 nm (log $\epsilon$=4.91; E=2045).

Microanalysis: Calc.: C 81.77% H 10.17% Found: C 81.50% H 9.84%

EXAMPLE 3

8'-Apo-β-Carotenal Dimethyl Acetal 6.25 g (15 mmol) of 8'-apo-β-carotenal and 6.6 ml (6.4 g, 60 mmol, 4 eq.) of trimethyl orthoformate in 200 ml of methanol were placed in a 350 ml four-necked sulphonation flask equipped with a mechanical stirrer, argon gasification and a thermometer. A solution of 20 mg of p-toluenesulphonic acid monohydrate in 10 ml of methanol was added thereto at room temperature and the mixture was stirred for 2½ hours. Thereby, the red crystals dissolved slowly and an orange crystallizate began to form. Then 2 ml of triethylamine were added, the mixture was cooled to 0° C. within about 30 minutes and suction filtered, and the solid was washed with a small amount of cold (−10° C.) methanol and dried briefly under reduced pressure (water-jet vacuum). After 30 minutes this gave 11.6 g of methanol-moist acetal with a content of 94.8% according to HPLC. For recrystallization, the crystals were dissolved in 200 ml of diethyl ether and then 600 ml of methanol were added thereto within 1½ hours, the mixture was cooled to 0° C. and the crystals were filtered off and dried at room temperature under reduced pressure (water-jet vacuum) and briefly under a high vacuum. This gave 5.9 g (84% yield) of 8'-apo-β-carotenal dimethyl acetal as rust-red crystals with m.p. 131°–132° C.; content according to HPLC: 98.4%; UV (n-hexane): 450 nm (log $\epsilon$=5.06; E=2476), 424 nm (log $\epsilon$=5.07; E=2543).

Microanalysis: Calc.: C 83.06% H 10.02% Found: C 82.91% H 10.13%

EXAMPLE 4

4'-Apo-β-Carotenal Dimethyl Acetal 10 g (20.7 mmol) 4'-apo-β-carotenal and 35 ml (0.31 mol, about 15 eq.) of trimethyl orthoformate in 250 ml of methanol were placed in a 500 ml four-necked sulphonation flask equipped with a mechanical stirrer, argon gasification and a thermometer. A solution of 25 mg of p-toluenesulphonic acid monohydrate in 15 ml of methanol was added at room temperature to the resulting dark red suspension, the mixture was stirred at room temperature for 45 minutes, then at 30°–35° C. for 1½ hours; the dark red suspension changed to a brown suspension. Subsequently, 2 ml of triethylamine were added and the mixture was cooled to 0° C. The precipitated crude product was filtered off under suction, washed with a small amount of cold methanol and dried briefly at room temperature under reduced pressure. The thus-obtained methanol-moist product (about 17.8 g; content according to HPLC: 91%) was dissolved in 600 ml of diethyl ether with slight warming and treated at room temperature within 1 hour with 1 l of methanol (containing 2%o triethylamine). Then the mixture was suction filtered and the residue was washed with a small amount of cold (0° C.) methanol. This gave, after drying at room temperature and under reduced pressure for 2 hours, 9.3 g (80.5% yield) of 4'-apo-β-carotenal dimethyl acetal as violet crystals with a content of 94.7% according to HPLC.

For the analytical data, a sample was recrystallized from diethyl ether (dissolved while warming and cooled to 0° C.): content according to HPLC: 95.7%; m.p. 186°–188° C.; UV (dioxan): 500 nm (log $\epsilon$=4.93; E=1623), 468 nm (log $\epsilon$=4.99; E=1837), 283 nm (log $\epsilon$=4.37; E=444).

EXAMPLE 5

12,12'-Diapocarotenal Dimethyl Acetal ($C_{10}$-Dialdehyde Dimethyl Acetal)

32.8 g (0.2 mol) of $C_{10}$-dialdehyde and 65 g of trimethyl orthoformate in 250 ml of methanol were placed in a 500 ml round flask equipped with a magnetic stirrer and argon gasification. 100 mg of p-toluenesulphonic acid monohydrate were added thereto at about 20° C., which produced a slightly exothermic reaction. The reaction mixture was held at about 20°–25° C. using a cold water bath. The suspension dissolved in about 5 minutes. Then the mixture was stirred at room temperature for one hour and about 0.5 ml of triethylamine was subsequently added. The mixture was concentrated under reduced pressure and the separated crystal slurry was dissolved in 200 ml of hot n-hexane, filtered while hot through cotton wool and left to stand. The solution was left to stand at −20° C. in a deep freezer for about 16 hours, the resulting crystals were filtered off, washed with n-hexane at -20° C. and dried to constant weight under a water-jet vacuum. This gave 42.7 g (80% yield) of $C_{10}$-dialdehyde dimethyl acetal as pale yellow crystals with m.p. 68°–69° C. and a content according to gas chromatography (GC) of about 96%; UV (ethanol): 292 nm (log $\epsilon$=4.61; E=1602), 280 nm (log $\epsilon$=4.72; E=2046), 260 nm (log $\epsilon$=4.59; E=1508).

Microanalysis: Calc.: C 65.60% H 9.44% Found: C 65.43% H 9.14%

EXAMPLE 6

8,8'-Diapocarotenal Dimethyl Acetal (Crocetin Dialdehyde Dimethyl Acetal)

20.0 g (67.5 mmol) of crocetin dialdehyde (m.p. 196°–197° C.) and 40 g (0.37 mol) of trimethyl orthoformate in 350 ml of methanol were placed in a 500 ml round flask equipped with a magnetic stirrer and argon gasification. 200 mg of p-toluenesulphonic acid monohydrate were added thereto at room temperature while stirring and the mixture was stirred at room temperature for about 45 minutes and at 35°–40° C. for about 1½ hours, which gave a yellow-orange suspension. Then the mixture was cooled to 0° C., filtered and the residue was washed with cold methanol (−10° C.). This gave 24.7 g (92% yield) of crocetin dialdehyde dimethyl acetal as an orange powder, m.p. 136° C., with a content of 97.4% according to HPLC. Recrystallization from 150 ml of hot ethyl acetate and 150 ml of methanol while cooling to −20° C. gave, after filtration and drying (water-jet vacuum, followed by high vacuum), 23.3 g (86% yield) of crocetin dialdehyde dimethyl acetal as rust-red crystals, m.p. 138°–139° C., with a content of 97.3% according to HPLC; UV (ethanol): 422 nm (log $\epsilon$=5.12; E=3416), 397 nm (log $\epsilon$=5.11; E=3305), 377 nm (log $\epsilon$=4.89; E=1985), 232 nm (log $\epsilon$=4.20; E=405).

Microanalysis: Calc.: C 74.19% H 9.34% Found: C 74.10% H 9.47%

B. Production of vinylketene acetals or analogues thereof (compounds of formula III)

EXAMPLE 7

1,1-Dimethoxy-2-Methyl-1,3-Butadiene [Three Steps a), b) and c)]

a) 2-Methyl-3-buteniminoic acid methyl ester hydrochloride 173 g (220 ml, 5.4 mol, 1.1 eq.) of methanol in 2.5 l of toluene and 2.5 l of n-hexane were placed in a 6 l four-necked sulphonation flask equipped with a mechanical stirrer, a thermometer and a gas inlet tube (for argon gasification). 216 g (5.92 mol, 1.2 eq.) of gaseous hydrogen chloride (dried over concentrated sulphuric acid) were introduced at 0° C. (bath temperature −10° C.) and while stirring within 1½ hours. Then 500 g (4.9 mol, 1 eq.) of 80% 2-methyl-3-butenenitrile were added thereto at between 0° and 5° C. within 45 minutes, the ice bath was replaced by a cool (20° C.) water bath and the mixture was stirred further at room temperature for about 20 hours. The separated precipitate was cooled (ice bath) for 1 hour, filtered off under suction, washed with 1 l of n-hexane and dried at room temperature for 18 hours under reduced pressure (water-jet vacuum). This gave 594 g (81% yield) of 2-methyl-3-buteniminoic acid methyl ester hydrochloride with m.p. 106° C. (with decomposition).

b) 2-Methyl-3-butenoic acid orthomethyl ester 297 g (2 mol) of 2-methyl-3-buteniminoic acid methyl ester hydrochloride were dissolved at room temperature in 1 l of methanol in a Kutscher-Steudel apparatus (2.5 l content, 1 l round flask for pentane collection). This solution was then extracted continuously with 2 l of n-pentane over about 24 hours, with the methanol phase being stirred magnetically. Thereby, ammonium chloride separated. Subsequently, the pentane in the round flask (about 600–700 ml) was concentrated. This gave 234 g of crude 2-methyl-3-butenoic acid orthomethyl ester with a content of 66% according to GC.

A repetition of this procedure on the same scale gave 236 g of crude product with a content of 70% according to GC. The two crude products were combined (total 470 g) and fractionated at 30 mbar on a Vigreux column (20 cm, metallized). 310 g (43% yield) of 2-methyl-3-butenoic acid orthomethyl ester with a content of 89.5% according to GC were obtained at a boiling temperature of 65°–66° C./30 mbar.

c) 1,1-Dimethoxy-2-methyl-1,3-butadiene

About 600 ml of liquid ammonia were condensed at −70° C. using an ascending tube in a 1.5 l four-necked sulphonation flask equipped with a mechanical stirrer, a thermometer, a dropping funnel and argon gasification. 1 spatula tip of iron(III) nitrate was added to the condensate. Thereafter, 21 g (0.91 mol, 3.2 eq.) of sodium metal were added within 30 minutes and the mixture was stirred at −45° to −65° C., which gave a dark grey suspension. A solution of 50.8 g (0.284 mol) of 2-methyl-3-butenoic acid orthomethyl ester with a content of 89.5% according to GC in 200 ml of diethyl ether was then added dropwise at −45° to −40° C. within 1 hour, and the mixture was subsequently stirred at −45° C./1 hour. Thereafter, the cooling was removed and the ammonia was evaporated within 2 hours (water bath/20° C.). After the addition of 200 ml of diethyl ether 100 ml of water were cautiously added dropwise at between 0° and 20° C., the aqueous phase was separated and again extracted twice with two 150 ml portions, a total of 300 ml, of n-pentane. After the addition of 40 mg of 2,6-di-tert.butyl-p-cresol the combined extracts were dried over anhydrous sodium sulphate and concentrated cautiously at 25°–30° C. under reduced pressure. This gave 37.3 g of crude 1,1-dimethoxy-2-methyl-1,3-butadiene with a content of 95% according to GC. Distillation on a 10 cm Vigreux column at 20 mbar gave, at a boiling temperature of 48° C., 34.2 g (90.2% yield) of 1,1-dimethoxy-2-methyl-1,3-butadiene with a content of 96% according to GC as a colourless liquid, which, after the addition of 35 mg (1‰) of 2,6-di-tert.butyl-p-cresol, was stored at 0° C. under argon.

EXAMPLE 8

(E/Z)-1-Trimethylsilyloxy-1-Ethoxy-2-Methyl-1,3-Butadiene 25.6 ml (181 mmol, 1.1 eq.) of diisopropylamine in 160 ml of tetrahydrofuran (distilled over LiAlH$_4$) were placed in a 500 ml four-necked sulphonation flask equipped with a mechanical stirrer, a thermometer, two dropping funnels and argon gasification. 113 ml (181 mmol, 1.1 eq.) of a butyl-lithium solution (1.6M in n-hexane) were added dropwise thereto at −25° C. within 45 minutes, the mixture was then cooled to −70° C. and a solution of 21.2 g (165 mmol) of ethyl 2-methyl-3-butenoate [see German Offenlegungsschrift 3,244,273 as well as U.S. Pat. No. 4,937,308] with a content of 100% according to GC in 30 ml of absolute tetrahydrofuran (distilled over LiAlH$_4$) was added dropwise thereto within 30 minutes. Then the mixture was stirred for 20 minutes at −70° C. and subsequently at this temperature 25.1 ml (=21.6 g, 0.199 mol, 1.2 eq.) of trimethylchlorosilane were added dropwise thereto. The cooling bath was now removed, so that the temperature rose from −70° C. to room temperature within about 2½ hours. Then the mixture was suction filtered over Celite® (a filter aid consisting of kieselguhr; Manville Corp., USA), rinsed with tetrahydrofuran, a small amount (about 100 mg) of 2,6-di-tert.butyl-p-cresol was added and the mixture was concentrated cautiously at 40° C. under reduced pressure. The residue was taken up in n-pentane and the solution was filtered and concentrated. Distillation under a high vacuum (0.25 mbar) gave, at a boiling temperature of 28° C. (while cooling well), 25.8 g (73% yield) of (E/Z)-1-trimethylsilyloxy-1-ethoxy-2-methyl-1,3-butadiene with a content of 94% according to GC.

EXAMPLE 9

2-(1-Methyl-Allylidene)-[1,3]Dioxolane [Two Steps a) and b)]

a) 2-Methyl-but-3-enoic acid 2-chloroethyl ester 45.1 g (0.45 mol) of 2-methyl-3-butenoic acid, 45.33 g (0.56 mol) of 2-chloroethanol and 4.1 g (34 mmol) of dimethyl-aminopyridine were placed in 450 ml of diethyl ether under argon. 102.2 g (0.495 mol) of N,N-dicyclohexylcarbodiimide were added thereto in 5 portions at 0° C. within 30 minutes, the mixture was stirred at room temperature for a further 2 hours and the separated urea was filtered off. The filtrate was washed in succession with 200 ml of 0.5N aqueous hydrochloric acid, 100 ml of saturated sodium bicarbonate solution and 100 ml of saturated sodium chloride solution. The organic solution was dried over anhydrous 2 0 sodium sulphate and, after concentration, the product was distilled on a Vigreux column (20 cm) at 80°–81° C./10 mbar. This gave 62.3 g (83% yield) of 2-methyl-but-3-enoic acid 2-chloroethyl ester as a colourless oil with a content of 97.5% according to GC.

b) 2-(1-Methyl-allylidene)-[1,3]dioxolane 90.6 g (about 113 ml) of 20% potassium hydride in oil (density about 0.8) were washed twice with n-hexane under argon, and then treated with 700 ml of dimethoxyethane. Subsequently, a solution of 56.5 g (0.34 mol) of 2-methyl-but-3-enoic acid 2-chloroethyl ester with a content of 97.5% according to GC in 175 ml of dimethoxyethane was added thereto while stirring at 20° C. within 1½ hours, and the mixture was stirred at room temperature for 1 hour. 250 ml of water were cautiously added dropwise thereto at 0°–5° C. The aqueous phase was then separated and extracted three times with three 300 ml portions, a total of 900 ml, of n-hexane. Washing of the combined organic phases with 250 ml of saturated sodium chloride solution, drying and concentration gave a yellow liquid (50.5 g; GC: 83.4%), which, after the addition of 40 mg of 2,6-di-tert.butyl-p-cresol, was fractionated on a Vigreux column (20 cm). This gave, at a boiling temperature of 93°–94° C./19 mbar, 28.22 g (66% yield) of 2-(1-methyl-allylidene)-[1,3]dioxolane as a colourless oil with a content of 100% according to GC.

C. Production of the compounds of formulas IV' and IV" from the polyene (di)O,O-dialkyl acetals of formula II and II", respectively, and the vinylketene acetals or analogues thereof of formula III

EXAMPLE 10

15-Methoxy-15,15'-Dihydro-12'-β-Carotenoic Acid Ethyl Ester 1.75 g (5 mmol) of vitamin A aldehyde dimethyl acetal (HPLC: 98%) and 1.5 g (6.5 mmol) of (E/Z)-1-trimethylsilyloxy-1-ethoxy-2-methyl-1,3-butadiene (GC: 87%) in 20 ml of tert.butyl methyl ether were placed in a 50 ml four-necked sulphonation flask equipped with a thermometer, a magnetic stirrer and argon gasification. 7 drops (=about 80 mg, 10 mol %) of boron trifluoride etherate were added thereto at −30° C. within 20 minutes. After 1 hour [tlc (SiO$_2$): R$_f$=about 0.3; cyclohexane/ethyl acetate (9:1)] 1 ml of triethylamine was added at −30° C. and the mixture was warmed to room temperature and poured into 20 ml of water. The separated aqueous phase was extracted twice with 20 ml portions, a total of 40 ml, of n-hexane and the combined organic phases were washed with 20 ml of saturated sodium chloride solution, dried over anhydrous sodium sulphate and concentrated. Chromatographic purification of the yellow, oily crude product (2.7 g) on 100 g of silica gel (0.04–0.063 mm) with cyclohexane/ethyl acetate (9:1) gave 1.68 g (74% yield) of 15-methoxy-15,15'-dihydro-12'-β-carotenoic acid ethyl ester as a thick yellow oil (content according to HPLC: 97%); UV (n-hexane): 325 nm (log ε=4.63; E=989).

EXAMPLE 11

15-Methoxy-15,15'-Dihydro-12'-Apocarotenoic Acid Methyl Ester 1.75 g (5 mmol) of vitamin A aldehyde dimethyl acetal (HPLC: 98%) and 0.8 g (6.5 mmol, 1,3 eq.) of 1,1-dimethoxy-2-methyl-1,3-butadiene (GC: 99%) in 20 ml of tert.butyl methyl ether were placed in a 50 ml flask under argon. 5 drops (about 60 mg, 8 mol %) of boron trifluoride etherate were added thereto while stirring at −30° C. and the mixture was stirred further at about −30° C. (initially a very dark coloured solution, which lightened to an orange solution after about 10 minutes: tlc (SiO$_2$): R$_f$=about 0.3; n-hexane/ethyl acetate=9:1).

For the hydrolysis, 5 ml of acetic acid/water (9:1) were then added at −30° C. and the mixture was stirred at 0° C. for 20 minutes. Then 20 ml of water were added, the mixture was extracted with two 20 ml portions, a total of 40 ml, of n-hexane and the combined organic phases were washed once with 20 ml of saturated sodium bicarbonate solution and once with sodium chloride solution, dried over anhydrous sodium sulphate and concentrated under reduced pressure. The crude product (2.5 g) was chromatographed on 125 g of silica gel (0.040–0.063 mm) with n-hexane/ethyl acetate (9:1). This gave 1.50 g (69% yield) of 15-methoxy-15,15'-dihydro-12'-apocarotenoic acid methyl ester as a yellow oil; content according to HPLC: 95.2%; UV (n-hexane): 325 nm (log ε=4.67; E=1132).

Microanalysis: Calc.: C 78.60% H 9.77% Found: C 78.26% H 10.08%

In this chromatography there could be isolated in an early fraction 130 mg (about 6%) of (13-cis)-15-methoxy-15,15'-dihydro-12'-apocarotenoic acid methyl ester as a yellow oil; content according to HPLC: 95.3%; UV (n-hexane): 329 nm (log ε=4.58; E=926).

EXAMPLE 12

12'-Methoxy-11',12'-Dihydro-8'-Apo-β-Carotenoic Acid Ethyl Ester 495 mg (1.25 mmol) of 12'-apo-β-carotenal dimethyl acetal and 325 mg (1.5 mmol) of (E/Z)-1-trimethylsilyloxy-1-ethoxy-2-methyl-1,3-butadiene (GC: 92%) in 5 ml of tert.butyl methyl ether were placed in a 10 ml round flask under argon. 17 mg (10 mol %) of anhydrous zinc chloride were added thereto at 0° C. and the mixture was stirred at +5° C. for 2 hours [tlc(SiO$_2$): R$_f$=about 0.2; toluene]. The orange-red reaction mixture was poured into 20 ml of water and extracted with two 20 ml portions, a total of 40 ml, of n-hexane, dried over anhydrous sodium sulphate and concentrated under reduced pressure. The crude product (760 mg) was chromatographed on 30 g of silica gel (0.040–0.063 mm) with toluene. This gave 609 mg (93% yield) of (all-E)-12'-methoxy-11',12'-dihydro-8'-apo-β-carotenoic acid ethyl ester as a viscous orange oil; content according to HPLC: 94%. The spectroscopic data came from an analogous batch: UV (n-hexane): 395 nm (log ε=4.81; E=1300), 376 nm (log ε=4.82; E=1339).

Microanalysis: Calc.: C 80.44% H 9.82% Found: C 80.49% H 10.15%

EXAMPLE 13

12'-Methoxy-11',12'-Dihydro-8'-Apo-β-Carotenoic Acid Methyl Ester 6.2 g (15 mmol) of 12'-apo-β-carotenal dimethyl acetal and 3.1 g (24 mmol, 1.6 eq.) of 1,1-dimethoxy-2-methyl-1,3-butadiene (GC: 100%) in 60 ml of tert.butyl methyl ether were placed at −25° C. under argon in a 100 ml round flask. 80 mg (about. 6 drops, 4 mol %) of boron trifluoride etherate were added thereto at −25° C. while stirring and the mixture was stirred at −25° C. for 1 hour [tlc (SiO$_2$): R$_f$=about 0.25; toluene]. Then 15 ml of acetic acid/water (9:1) were added thereto and the mixture was stirred at room temperature for 30 minutes. Then the mixture was poured into 100 ml of tert.butyl methyl ether, washed with four 100 ml portions, a total of 400 ml, of water and the aqueous phases were extracted with 100 ml of tert.butyl methyl ether. The organic phases were combined, washed with 100 ml of saturated sodium bicarbonate solution and 100 ml of saturated sodium chloride solution, dried over anhydrous sodium sulphate, filtered and evaporated under reduced pressure. The separated dark oil (9.2 g) was chromatographed on 250 g of silica gel (0.040–0.063 mm) with toluene/ethyl acetate (19:1). This gave 6.9 g (89% yield) of 12'-methoxy-11',12'-dihydro-8'-apo-β-carotenoic acid methyl ester as a red-orange, viscous oil with a content of 93.1% according to HPLC. UV (cyclohexane with 3% chloroform): 398 nm (log ε=4.77; E=1225), 380 nm (log ε=4.78; E=1257).

Microanalysis: Calc.: C 80.29% H 9.69% Found: C 80.45% H 9.53%

EXAMPLE 14

12'-Methoxy-11,12'-Dihydro-8'-Apo-β-Carotenoic Acid 2-Hydroxyethyl Ester 2.98 g (7.3 mmol) of 12'-apo-β-carotenal dimethyl acetal (content according to HPLC: about 97%) and 1.42 g (11.25 mmol) of 2-(1-methyl-allylidene)-[1,3]dioxolane (GC: 100%) in 30 ml of tert.butyl methyl ether were placed in a 100 ml round flask while gassing with argon. 2 drops (about 25 mg, 2 mol %) of boron trifluoride etherate were added thereto while stirring at −25° C. and the mixture was stirred at this temperature for 1 hour. Then 8 ml of acetic acid/water (9:1) were added thereto, the cooling was removed and the mixture was left to warm to room temperature within 30 minutes [R$_f$=about 0.4, n-hexane/ethyl acetate 1:1). The reaction mixture was then poured into 100 ml of tert.butyl methyl ether and washed twice with 150 ml of water each time, once with 100 ml of saturated sodium bicarbonate solution and once with 50 ml of saturated sodium chloride solution. Subsequently, the organic phase was dried over anhydrous sodium sulphate, filtered and concentrated, and the crude product (4.1 g) was chromatographed on 120 g of silica gel (0.040–0.063 mm) with n-hexane/ethyl acetate (1:1). After crystallization from n-hexane there were obtained 1.85 g (49%) of 12'-methoxy-11',12'-dihydro-8'-apo-β-carotenoic acid 2-hydroxyethyl ester as pale yellow crystals, m.p. 98°–100° C., with a content of 97.6% according to HPLC. UV (n-hexane): 395 nm (log ε=4.92; E=1634), 377 nm (log ε=4.93; E=1669).

A resinous byproduct (65 mg), presumably having the following structure (according to $^1$H-NMR and mass spectrum) could be isolated from the mother liquor of the crystallization after chromatography on silica gel (eluent: toluene/ethyl acetate=8:2):

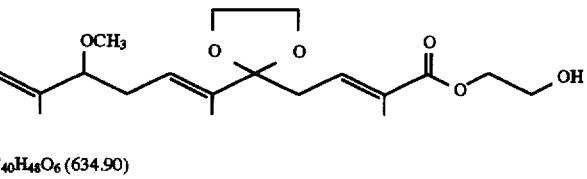

$C_{40}H_{48}O_6$ (634.90)

EXAMPLE 15

8'-Methoxy-7',8'-Dihydro-4'-Apo-β-Carotenoic Acid Ethyl Ester 4.73 g (10 mmol) of 8'-apo-β-carotenal dimethyl acetal (content according to HPLC: 98%) and 2.56 g (12 mmol, 1,2 eq.) of (E/Z)-1-trimethylsilyloxy-1-ethoxy-2-methyl-1,3-butadiene (GC: 94%) in 100 ml of tert.butyl methyl ether were placed in a 250 ml found flask while gassing with argon. 66 mg (0.5 mmol, 5 mol %) of anhydrous zinc chloride were added thereto at 0° C. and the mixture was stirred at room temperature for 3 hours [tlc (SiO$_2$): R$_f$=about 0.2; toluene]. Then 50 ml of water were added and, after separation, this was extracted with 50 ml of n-hexane. After drying over anhydrous sodium sulphate, filtration and evaporation of the solvent the separated red oil (5 g) was dissolved in 100 ml of ethanol while heating and slowly cooled to 0° C. The separated crystals were filtered off under suction, washed with a small amount of cold ethanol and dried at room temperature under a water-jet vacuum. This gave 3.8 g (65% yield) of 8'-methoxy-7',8'-dihydro-4'-apo-β-carotenoic acid ethyl ester as red crystals with m.p.

107°–108° C.; content according to HPLC: 96.4%; UV (n-hexane): 451 nm (log ε=5.04; E=1955), 425 nm (log ε=5.08; E=2146).

EXAMPLE 16

8'-Methoxy-7',8'-Dihydro-4'-Apo-β-Carotenoic Acid Methyl Ester 4.80 g (10 mmol) of 8'-apo-β-carotenal dimethyl acetal (content according to HPLC: 97%) and 2.20 g (17 mmol) of 1,1-dimethoxy-2-methyl-1,3-butadiene (GC: 99%) in 100 ml of tert.butyl methyl ether were placed in a 50 ml round flask while gassing with argon. One drop (12 mg) and then after 30 minutes a further one drop, a total of two drops (24 mg, about 2 mol %), of boron trifluoride etherate were added thereto at 0° C. while stirring and the mixture was stirred at 0° C. for 1 hour in total.

For the hydrolysis, 20 ml of acetic acid/water (9:1) were added at 0° C. to the mixture, which was stirred at room temperature for about 50 minutes [tlc (SiO$_2$): R$_f$=about 0.2; toluene]. Then the solution was placed in a separating funnel and washed with two 100 ml portions, a total of 200 ml, of water and 100 ml of saturated sodium bicarbonate solution. The aqueous phases were each extracted with 100 ml of n-hexane. Drying over anhydrous sodium sulphate, filtration and evaporation under reduced pressure gave 8.6 g of a thick oil, which was dissolved in 250 ml of ethanol while warming slightly. After cooling to 0° to −20° C., filtration and drying of the crystals there were obtained 3.0 g (53% yield) of 8'-methoxy-7',8'-dihydro-4'-apo-β-carotenoic acid methyl ester as orange crystals, m.p. 84°–86° C., with a content of 96.2% according to HPLC. UV (cyclohexane with 3% chloroform): 456 nm (log ε=4.77; E=1087), 430 nm (log ε=4.82; E=1225), 407 nm (log ε=4.67; E=855).

EXAMPLE 17

Isolation/characterization of the orthoester 8'-methoxy-7',8'-dihydro-4'-apo-β-carotenoic acid orthomethyl ester occurring as the intermediate (see Example 16: acid-catalyzed hydrolysis omitted)

EXAMPLE 18

4'-Methoxy-β,ψ-Caroten-16'-Oic Acid Ethyl Ester 2.91 g (5 mmol) of 4'-apo-β-carotenal dimethyl acetal (content according to HPLC: 91%) and 1.21 g (6 mmol) of 1-trimethylsilyloxy-1-ethoxy-2-methyl-1,3-butadiene (GC: 99%) in 50 ml of tert.butyl methyl ether were placed in a 150 ml round flask equipped with a magnetic stirrer and argon gasification and treated at 0° C. with 70 mg (0.5 mmol, 10 mol %) of anhydrous zinc chloride. Then the mixture was stirred at room temperature for about 18 hours [tlc (SiO$_2$): R$_f$=about 0.2; toluene], poured into water and worked-up as usual (see Example 10). This gave a dark red, viscous residue (5.4 g), which was chromatographed on 250 g of silica gel (0.04–0.063 mm) with toluene. A glutinous product (1.9 g, content according to HPLC: about 70%) was obtained. This residue was digested once in 40 ml of ethanol and once in 25 ml of hot (50° C.) ethanol, cooled (0° C.) and dried. This gave 0.86 g (26% yield) of 4'- methoxy-β,ψ-caroten-16'-oic acid ethyl ester as dark red crystals with m.p. 124°–125° C. and a content of 95.4% according to HPLC. UV (cyclohexane with 3% chloroform): 496 nm (log ε=4.98; E=1530), 464 nm (log ε=5.05; E=1790), 439 nm (log ε=4.91; E=1290).

EXAMPLE 19

4'-Methoxy-β,ψ-Caroten-16'-Oic Methyl Ester 2.91 g (5 mmol) of 4'-apo-β-carotenal dimethyl acetal (content according to HPLC: 91%) and 1.10 g (8.5 mmol) of 1,1-dimethoxy-2-methyl-1,3-butadiene (GC: 98%) were suspended in 50 ml of tert.butyl methyl ether in a 150 ml flask equipped with a magnetic stirrer and argon gasification. One drop (12 mg, 2 mol %) of boron trifluoride etherate was added thereto at 0° C. and the mixture was subsequently stirred at room temperature for 1 hour. Then 20 ml of acetic acid/water (9:1) were added and the mixture was stirred at room temperature for 2 hours [tlc (SiO$_2$): R$_f$=about 0.2;toluene]. Usual working-up (see Example 11) and chromatography of the residue on 250 g of silica gel (0.04–0.063

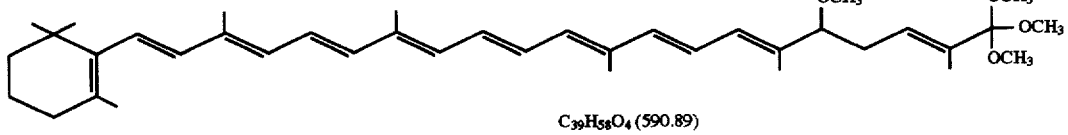

$C_{39}H_{58}O_4$ (590.89)

4.60 g (9.6 mmol) of 8'-apo-β-carotenal dimethyl acetal (content according to HPLC: 97%) and 1.95 g (15 mmol) of 1,1-dimethoxy-2-methyl-1,3-butadiene (GC: 99%) in 75 ml of tert.butyl methyl ether were placed in a 150 ml round flask while gassing with argon. One drop (12 mg, about 1 mol %) of boron trifluoride etherate was added at 0° C. below the reaction suspension. After a short time a dark red reaction solution formed, from which orange crystals separated. Stirring at 0° C. for ten minutes, suction filtration, washing of the solid with a small amount of a cold methanol/water (9:1) mixture and drying under a water-jet vacuum and subsequently under a high vacuum at room temperature gave 3.50 g (61% yield) of 8'-methoxy-7',8'-dihydro-4'-apo-β-carotenoic acid orthomethyl ester as orange crystals, m.p. 131°–132° C. UV (cyclohexane with 3% chloroform): 456 nm (log ε=5.04; E=1855), 430 nm (log ε=5.08; E=2047), 410 nm (log ε=4.91; E=1362).

Microanalysis: Calc.: C 79.28% H 9.89% Found: C 79.09% H 9.86% mm) with toluene gave a glutinous, dark red residue (2.2 g), which was digested in 60 ml of hot ethanol (50° C.). After cooling to 0° C., filtration and drying there was obtained 0.90 g (28% yield) of 4'-methoxy-β,ψ-caroten-16'-oic acid methyl ester as dark red crystals with m.p. 120°–123° C. and a content of 98.0% according to HPLC. UV (cyclohexane with 3% chloroform): 469 nm (log ε=5.10; E=2058), 465 nm (log ε=5.16; E=2220), 440 nm (log ε=4.99; E=1610).

EXAMPLE 20

12'-Methoxy-11,12'-Dihydro-8'-Apo-β-Caroten-8'-Oic Acid 2.97 g (7.3 mmol) of 12'-apo-β-carotenal dimethyl acetal (content according to HPLC: about 97%) and 2.63 g (9.7 mmol) of 1,1-bis(trimethylsilyloxy)-2-methyl-1,3-butadiene (content according to GC: 90.5%) in 30 ml of tert.butyl methyl ether were placed while gassing with argon in a 100 ml round flask equipped with a magnetic stirrer. 100 mg (0.7 mmol, 10 mol %) of anhydrous zinc chloride were added thereto at 0° C. and the mixture was stirred at this temperature for a further 5 hours. Then the reaction solution was poured into water, which caused the immediate hydrolysis of the intermediate of formula V', and extracted as usual (see Example 12). This gave a red resin (4.5 g), which was chromatographed on 200 g of silica gel (0.04–0.063 mm) with toluene/ethyl acetate (3:1). There were obtained 1.90 g (50% yield) of 12'-methoxy-11,12'-dihydro-8'-apo-β-caroten-8'-oic acid as a glutinous, orange-red foam (content after methylation with diazomethane and according to HPLC: 88.6%); UV (cyclohexane with 5% chloroform): 398 nm (log $\epsilon$=4.71; E=1100), 379 nm (log $\epsilon$=4.72; E=1340).

EXAMPLE 21

11,12,11',12'-Tetrahydro-12,12'-Dimethoxy-8,8'-Diapocarotene-8,8'-Dioic Acid Ethyl Ester 3.85 g (14.4 mmol) of 12,12'-diapocarotenal dimethyl acetal (m.p. 68°–69° C.; GC: 96%) and 7.84 g (36 mmol) of 1-trimethylsilyloxy-1-ethoxy-2-methyl-1,3-butadiene (content according to GC: 94%) in 60 ml of tert.butyl methyl ether were placed while gassing with argon in a 100 ml two-necked round flask equipped with a thermometer. 100 mg (0.7 mmol, 5 mol %) of anhydrous zinc chloride were added thereto at 0° C. and the mixture was stirred at room temperature for about 16 hours [tlc (SiO$_2$): R$_f$=about 0.2–0.3; n-hexane/ethyl acetate (4:1)]. 200 mg of 2,6-di-tert.butyl-p-cresol and then 25 ml of water were added to the yellowish reaction mixture, which was stirred at room temperature for 5 minutes, and the aqueous phase was separated and extracted twice with 50 ml, a total of 100 ml, of tert.butyl methyl ether. The combined organic phases were washed with 50 ml of saturated sodium bicarbonate solution and 50 ml of saturated sodium chloride solution, dried over anhydrous sodium sulphate and concentrated under reduced pressure. The separated oil (about 10 g) was chromatographed on 250 g of silica gel (0.04–0.063 mm) with n-hexane/ethyl acetate (4:1). This gave 6.28 g (93% yield) of 11,12,11',12'-tetrahydro-12,12'-dimethoxy-8,8'-diapocarotene-8,8'-dioic acid ethyl ester as a yellow oil (isomer mixture: mixture of two diastereomeric enantiomer pairs; content according to HPLC: 96.1%); UV (ethanol): 298 nm (log $\epsilon$=4.61; E=904), 289 nm (log $\epsilon$=4.72; E=1170), 276 nm (log $\epsilon$=4.59; E876).

Microanalysis: Calc.: C 69.61% H 8.99% Found: C 69.79% H 8.84%

EXAMPLE 22

11,12,11',12'-Tetrahydro-12,12'-Dimethoxy-8,8'-Diapocarotene-8,8'-Dioic Acid Methyl Ester 3.85 g (14.4 mmol) of 12,12'-diapocarotenal dimethyl acetal (m.p. 68°–69° C.; GC: 96%) and 5.37 g (40 mmol, 2.7 eq.) of 1,1-dimethoxy-2-methyl-1,3-butadiene (content according to GC: 94.5%) in 75 ml of tert.butyl methyl ether were placed in a 100 ml two-necked round flask equipped with a thermometer. On two occasions 6 drops, a total of 12 drops (about 140 mg, 7 mol %), of boron trifluoride etherate were added thereto within one hour at −20° C. and the mixture was stirred at −20° C. for 2 hours [tlc (SiO$_2$): R$_f$=about 0.2; n-hexane/ethyl acetate (4:1)]. Then 20 ml of acetic acid/water (9:1) were added, the mixture was stirred at 0° C. for 20 minutes, poured into 50 ml of water and worked-up analogously to Example 21. The separated yellow oil (7.1 g) was chromatographed on 250 g of silica gel (0.04–0.063 mm) with n-hexane/ethyl acetate (4:1). This gave 5.15 g (85% yield) of 11,12,11',12'-tetrahydro-12,12'-dimethoxy-8,8'-diapocarotene-8,8'-dioic acid methyl ester (mixture of two diastereomeric enantiomer pairs) as a yellow oil; content according to HPLC: 99.6%. A sample crystallized from n-hexane was used for the analysis: m.p. 68°–71° C.; content according to HPLC: 99.7%; UV (chloroform): 301 nm (log $\epsilon$=4.58; E=901), 289 nm (log $\epsilon$=4.69; E=1157).

Microanalysis: Calc.: C 68.55% H 8.63% Found: C 68.18% H 8.58%

EXAMPLE 23

7,8,7',8'-Tetrahydro-8,8'-Dimethoxy-4,4'-Diapocarotene-4,4'-Dioic Acid Ethyl Ester 2.54 g (7.5 mmol) of crocetin dialdehyde dimethyl acetal (content according to HPLC: 97.3%) and 4.79 g (22.5 mmol, 3 eq.) of 1-trimethylsilyloxy-1-ethoxy-2-methyl-1,3-butadiene (GC: 94%) in 60 ml of tert.butyl methyl ether were placed in a 150 ml round flask while gassing with argon. 105 mg (0.75 mmol, 10 mol %) of anhydrous zinc chloride were added thereto at 0° C. and the mixture was stirred at room temperature for about 16 hours [tlc (SiO$_2$): R$_f$=about 0.3; cyclohexane/ethyl acetate (4:1)]. Working-up was effected analogously to Example 21 and, after evaporation of the solvent, gave 3.83 g of crude 7,8,7',8'-tetrahydro-8,8'-dimethoxy-4,4'-diapocarotene-4,4'-dioic acid ethyl ester (mixture of two diastereomeric enantiomer pairs) as an orange oil. For purification, this crude product was dissolved in 10 ml of hot methanol and crystallized out at 0° C. for about 16 hours. This gave 2.20 g (49.4% yield) of product (as a mixture of two diastereomeric enantiomer pairs) as an orange crystalline powder, m.p. 61°–65° C.; content according to HPLC: 97.8%. Analysis was effected on a product with m.p. 63°–80° C. which was prepared, chromatographed and crystallized analogously; content according to HPLC: 98.4%; UV (cyclohexane with 3% chloroform): 428 nm (log $\epsilon$=5.02; E=1811), 402 nm (log $\epsilon$=5.01; E=1779), 381 nm (log $\epsilon$=4.79; E=1074).

EXAMPLE 24

7,8,7',8'-Tetrahydro-8,8'-Dimethoxy-4,4'-Diapocarotene-4,4'-Dioic Acid Methyl Ester 2.91 g (8.4 mmol) of crocetin dialdehyde dimethyl acetal (content according to HPLC: 97.3%) and 3.92 g (30 mmol, 3 eq.) of 1,1-dimethoxy-2-methyl-1,3-butadiene (GC: 98%) in 60 ml of tert.butyl methyl ether were placed while gassing with argon in a 100 ml flask equipped with a thermometer. At intervals of 10 minutes 4 separate drops (total about 50 mg, 4 mol %) of boron trifluoride etherate were added thereto at 0° C. After a further 30 minutes at 0° C. a further 2 drops (about 25 mg, 2 mol %) of boron trifluoride etherate were added. After a further hour at 0° C. 20 ml of acetic acid/water (9:1) were added, the mixture was stirred at 0° C. for 20 minutes, poured into 50 ml of water and worked-up analogously to Example 21 [tlc (SiO$_2$): R$_f$=about 0.3 (product); R$_f$=about 0.25 (educt); cyclohexane/ethyl acetate (4:1)]. This gave 6.5 g of crude product, which was chromatographed on 200 g of silica gel (0.04–0.063 mm) with n-hexane/ethyl acetate (4:1). There were obtained 3.05 g of 7,8,7',8'-tetrahydro-8,8'-dimethoxy-4,4'-diapocarotene-4,4'-dioic acid methyl ester as an orange solid, m.p. 73°–77° C.;

content according to HPLC: 84.7%. For further purification, recrystallization was carried out from 15 ml of hot ethanol after cooling to 0° to −20° C. This gave 2.4 g (51% yield) of 7,8,7',8'-tetrahydro-8,8'-dimethoxy-4,4'-diapocarotene-4, 4'-dioic acid methyl ester (mixture of two diastereomeric enantiomer pairs) as orange crystals, m.p. 83°–84° C.; content according to HPLC: 98.7%; UV (cyclohexane with 3% chloroform): 428 nm (log ε=5.05; E=2045), 402 nm (log ε=5.04; E=1996), 381 nm (log ε=4.82; E=1209).

EXAMPLE 25

Isolation/characterization of the bis-orthoester 7,8,7',8'-tetrahydro-8,8'-dimethoxy-4,4'-diapocarotene-4,4'-dioic acid orthomethyl ester occurring as the intermediate (see Example 24: acid-catalyzed hydrolysis excluded)

water at room temperature and once again with 50 ml of methanol at −20° C., and finally dried at 30° C. under a water-jet vacuum and then at room temperature under a high vacuum. This gave 2.30 g (63% yield) of 12'-apo-β-carotenoic acid ethyl ester as an orange powder, m.p. 80°–81° C.; content according to HPLC: 95%; UV (n-hexane): 398 nm (log ε=4.90; E=2028).

Microanalysis: Calc.: C 82.18% H 9.71% Found: C 82.03% H 9.75%

EXAMPLE 27

12'-Apo-β-carotenoic Acid Methyl Ester 1.36 g (3.25 mmol) of 15-methoxy-15,15'-dihydro-12'-apocarotenoic acid methyl ester in 20 ml of methanol were

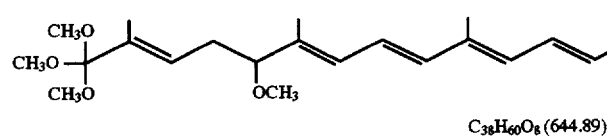
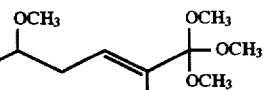

$C_{38}H_{60}O_8$ (644.89)

1.94 g (5.6 mmol) of crocetin dialdehyde dimethyl acetal (content according to HPLC: 97.3%) and 2.0 g (15.5 mmol) of 1,1-dimethoxy-2-methyl-1,3-butadiene (GC: 99.5%) in 40 ml of tert.butyl methyl ether were treated at 0° C. in a 100 ml round flask while gassing with argon with 140 mg (1 mmol) of anhydrous zinc chloride and stirred at room temperature for about 16 hours [tlc (SiO₂): R$_f$=about 0.15 (product); R$_f$=0.25 (educt); cyclohexane/ethyl acetate (4:1)]. For the working-up, the mixture was poured into water and extracted with ethyl acetate. This gave, after evaporation under reduced pressure, a crude product (4.8 g), which was dissolved in n-hexane/ethyl acetate (6:1). After cooling to 0° C. a yellow product separated and this was filtered off (0.9 g), dissolved in 45 ml of warm methanol and cooled to 0° to −20° C. This gave 0.59 g (about 16% yield) of 7,8,7',8'-tetrahydro-8,8'-dimethoxy-4,4'-diapocarotene-4,4'-dioic acid orthomethyl ester as yellow crystals, m.p. 143°–147° C. Content according to HPLC: 96.8%; UV (cyclohexane with 3% chloroform): 428 nm (log ε=5.09; E=1920), 402 nm (log ε=5.08; E=1864), 381 nm (log ε=4.86; E=1116).

Microanalysis: Calc.: C 70.77% H 9.38% Found: C 70.84% H 8.98%

D. Manufacture of the Polyene Esters or Acids of Formulas I' and I" from the Compounds of Formulas IV' and IV", Respectively

EXAMPLE 26

12'-Apo-β-carotenoic Acid Ethyl Ester 3.80 g (8.75 mmol) of 15-methoxy-15,15'-dihydro-12'-apocarotenoic acid methyl ester in 15 ml of ethanol were placed in a 150 ml round flask while gassing with argon. A sodium ethylate solution, prepared by dissolving 0.64 g (27 mmol; 3 eq.) of sodium in 35 ml of ethanol, was added at room temperature and the mixture was stirred at 40° C. for 2 hours, giving a dark brown solution [tlc (SiO₂): R$_f$=about 0.5; cyclohexane/ethyl acetate (9:1)]. Then 1.2 ml (1.3 g, 21 mmol) of acetic acid were added at room temperature, whereupon a yellow suspension formed and was cooled to −40° C., stirred for 1½ hours and the solid was filtered off under suction. This was washed once with 20 ml of methanol at −20° C., twice with 50 ml portions, a total of 100 ml, of placed in a 100 ml round flask while gassing with argon. 10 ml (10 mmol) of a 1 molar solution of sodium methylate in methanol were added thereto at room temperature and the mixture was stirred at 50° C. for 3 hours, which gave a dark reaction solution [tlc (SiO₂): R$_f$=about 0.4–0.5; n-hexane/ethyl acetate (9:1)]. Then the mixture was cooled to 0° C. and 1.2 g (20 mmol) of acetic acid were added followed by 20 ml of water, whereupon an orange glutinous precipitation occurred. The suspension was washed with 75 ml of ethyl acetate into a separating funnel containing 50 ml of water. The aqueous phase was separated and extracted with 75 ml of ethyl acetate. After drying over anhydrous sodium sulphate the organic phase was concentrated under reduced pressure and the residue (1.8 g) was chromatographed on 50 g of silica gel (0.04–0.063 mm) with n-hexane/ethyl acetate (14:1). This gave 1.3 g of an orange oil, which was dissolved in 10 ml of ethanol and crystallized at 0° to −20° C. for about 16 hours. There was obtained 0.55 g (44% yield) of 12'-apo-β-carotenoic acid methyl ester as red crystals, m.p. 73°–83° C.; content according to HPLC: 98%. UV (n-hexane): 398 nm (log ε=4.90; E=2100).

Microanalysis: Calc.: C 82.06% H 9.54% Found: C 82.15% H 9.61%

EXAMPLE 28

8'-Apo-β-carotenoic acid ethyl ester (through process from 12'-apo-β-carotenal dimethyl acetal and 1-trimethylsilyloxy-1-ethoxy-2-methyl-1,3-butadiene via 12'-methoxy-11',12'-dihydro-8'-apo-β-carotenoic acid ethyl ester)

A solution of 12.40 g (30 mmol) of 12'-apo-β-carotenal dimethyl acetal (m.p. 78°–79° C.; HPLC: 96.5%) and 7.6 g (36 mmol, 1.2 eq.) of 1-trimethylsilyloxy-1-ethoxy-2-methyl-1,3-butadiene (content according to GC: 95%) in 120 ml of tert.butyl methyl ether was treated at 0° C. in a 300 ml round flask equipped with a magnetic stirrer and argon gasification with 80 mg (0.6 mmol, 2 mol %) of anhydrous zinc chloride and stirred at room temperature for about 16 hours [tlc (SiO₂): R$_f$(acetal)=about 0.3; R$_f$(product)=about 0.2; toluene]. Then 200 mg of 2,6-di-tert.butyl-p-cresol were added and the mixture was added to 50 ml of water. After separating the aqueous phase it was extracted with 50 ml of tert.butyl methyl ether, washed with 50 ml of saturated sodium bicarbonate solution and 50 ml of saturated sodium chloride solution, dried over anhydrous sodium sulphate, filtered and concentrated under reduced pressure. In order to remove remaining organic solvent and water, the oily residue was dissolved in 200 ml of absolute ethanol and concentrated under reduced pressure. This gave 17.4 g of crude 12'-methoxy-11',12'-dihydro-8'-apo-β-carotenoic acid ethyl ester as a red-orange sticky, ethanol-moist oil (content according to HPLC: 89.7%).

This oil was placed with 250 ml of absolute ethanol in a 500 ml four-necked sulphonation flask equipped with a mechanical stirrer, argon gasification, a thermometer and a dropping funnel. A sodium ethylate solution, prepared by dissolving 1.40 g (60 mmol, 2 eq.) of sodium in 70 ml of absolute ethanol, was added thereto at room temperature and the mixture was stirred at room temperature for about 16 hours. A precipitate began to form after about 1–2 hours. In order to complete the reaction, the thick precipitate was stirred at 40° C. for 4 hours [tlc (SiO$_2$): R$_f$=about 0.4; only traces of intermediate; toluene]. Then the mixture was cooled to 25° C. and a solution of 4.2 g (70 mmol) of acetic acid in 10 ml of ethanol was added dropwise followed by a mixture of 40 ml of ethanol and 42 ml of water within about 1 hour. The mixture was subsequently cooled to +5° C. with an ice bath and filtered, and the filter material was washed at 0° C. with 50 ml of ethanol/water (9:1) and at room temperature with three 50 ml portions, a total of 150 ml, of water and dried at room temperature under a high vacuum for 16 hours. This gave 12.50 g of crude 8'-apo-β-carotenoic acid ethyl ester as a brick-red powder with m.p. 136°–137° C.; content according to HPLC: 99.1% (all-E).

For further purification, 12.40 g of the above product were suspended in 100 ml of acetone and the suspension was refluxed while stirring. After refluxing for a quarter of an hour the product did not pass completely into solution. 5 ml of water were added dropwise to the refluxing suspension through the reflux condenser in about one minute while stirring, then the mixture was cooled slowly to 0° C., filtered and washed twice with two 20 ml portions, a total of 40 ml, of cold acetone/water (9:1) and twice with two 25 ml portions, a total of 50 ml, of water at −20° C. After drying at 45° C. under a water-jet vacuum to constant weight and at room temperature under a high vacuum (0.05 mmHg) there were obtained 11.00 g (80% yield) of 8'-apo-β-carotenoic acid ethyl ester as dark red glistening crystals with m.p. 139° C. and a content according to HPLC of 99.6%. UV (cyclohexane with 3% chloroform): 473 nm (log ε=4.98; E=2065), 447 nm (log ε=5.06; E=2481), 262 nm (log ε=4.25; E=385).

EXAMPLE 29

8'-Apo-β-carotenoic acid ethyl ester (through process from 12'-apo-β-carotenal dimethyl acetal and 1,1-dimethoxy-2-methyl-1,3-butadiene via 12'-methoxy-11',12'-dihydro-8'-apo-β-carotenoic acid methyl ester)

A solution of 6.20 g (15 mmol) of 12'-apo-β-carotenal dimethyl acetal (m.p. 78°–79° C.; HPLC: 96.5%) and 3.04 g (22.5 mmol) of 1,1-dimethoxy-2-methyl-1,3-butadiene (content according to GC: 95%) in 60 ml of tert.butyl methyl ether was treated at −25° C. while gassing with argon in a 100 ml round flask equipped with a magnetic stirrer with 80 mg (about 6 drops, about 0.6 mmol, 4 mol %) of boron trifluoride etherate. The colour of the solution changed to deep blue upon addition of the catalyst. The solution was stirred for about one hour [tlc (SiO$_2$): R$_f$ about 0.2 (toluene)]. For the hydrolysis, 15 ml of acetic acid/water (9:1) were added at −25° C. and the mixture was warmed to 0° C., stirred at room temperature for about 30 minutes and worked-up analogously to Example 21. This gave 10.0 g of crude 12'-methoxy-11',12'-dihydro-8'-apo-β-carotenoic acid methyl ester as a red, sticky, ethanol-moist oil, which was dissolved in 130 ml of ethanol in a 350 ml four-necked sulphonation flask equipped with a mechanical stirrer, a thermometer and argon gasification. After the addition of a sodium ethylate solution, prepared by dissolving 700 mg (30 mmol) of sodium in 35 ml of absolute ethanol, the mixture was stirred at room temperature for about 16 hours and at 50° C. for 1½ hours. Working-up was effected analogously to Example 28. This gave 6.1 g (86%) of 8'-apo-β-carotenoic acid ethyl ester as a red-violet powder, m.p. 140° C.; content according to HPLC: 97.5%. Recrystallization in acetone/water analogously to Example 28 gave 5.81 g (83% yield) of 8'-apo-β-carotenoic acid ethyl ester as violet, metallic-glistening crystals, m.p. 141° C.; content according to HPLC: 98.3%.

EXAMPLE 30

8'-Apo-β-carotenoic acid ethyl ester (through process from 12'-apo-β-carotenal dimethyl acetal and 2-(1-methyl-ethylidene)-[1,3]dioxolane via 12'-methoxy-11',12'-dihydro-8'-apo-β-carotenoic acid 2-hydroxyethyl ester)

16.4 g (40 mmol) of 12'-apo-β-carotenal dimethyl acetal (content according to HPLC: 96.8%) and 7.57 g (60 mmol) of 2-(1-methyl-allylidene)-[1,3]dioxolane (content according to GC: 100%) in 160 ml of ethyl acetate were placed in a 350 ml four-necked sulphonation flask while gassing with argon. 210 mg (4 mol %) of boron trifluoride etherate were added thereto at −25° C. and the mixture was stirred at this temperature for 1 hour. Then 40 ml of acetic acid/water (9:1) were added, the cooling was removed and the mixture was stirred at about 17° C. for a further 40 minutes [tlc (SiO$_2$): R$_f$=about 0.35; n-hexane/ethyl acetate (1:1)]. For the working-up, the reaction mixture was poured into 500 ml of ethyl acetate, washed with two 400 ml portions, a total of 800 ml, of water, once with 300 ml of saturated sodium bicarbonate solution and once with 150 ml of saturated sodium chloride solution. Then, the organic phase was dried over anhydrous sodium sulphate and concentrated. The oily residue was evaporated twice with in each case 250 ml, a total of 500 ml, of ethanol at 35° C. under reduced pressure. This gave a viscous orange-red oil (24 g), which was dissolved in 350 ml of ethanol and treated at room temperature in a 750 ml four-necked sulphonation flask equipped with a mechanical stirrer and while gassing with argon with a sodium ethylate solution prepared by dissolving 1.84 g (80 mmol) of sodium in 90 ml of ethanol. The mixture was stirred at room temperature for 16 hours and at 48° C. for 6 hours until practically no educt was detectable by tlc. A solution of 5.3 g (93 mmol) of acetic acid in 15 ml of ethanol was slowly added dropwise thereto at room temperature while stirring, followed by 120 ml of ethanol/water (1:1). Then the red crystal slurry was suction filtered, washed with 60 ml of ethanol/water (9:1) at 0° C. and washed at room temperature with 180 ml of water and at 0° C. with 50 ml of ethanol/water (9:1). After drying at 25 mbar and room temperature for 15 hours and at 45° C. under a high vacuum to about 0.16 mbar for 7 hours there were obtained 12.6 g (68.5%) of 8'-apo-β-carotenoic acid ethyl ester as brick-red crystals, m.p. 135° C. A recrystallization in acetone/water was effected analogously to Example 28 and gave 11.5 g (62%) of 8'-apo-β-carotenoic acid ethyl ester as violet, glistening crystals with m.p. 139.5° C. and a content according to HPLC of 99.5%.

EXAMPLE 31

8'-Apo-β-carotenoic Acid Methyl Ester 950 mg (41 mmol) of sodium were dissolved in 60 ml of methanol in a 500 ml round flask equipped with a magnetic stirrer, a condenser and argon gasification. A solution of 6.5 g (12.6 mmol) of 12'-methoxy-11',12'-dihydro-8'-apo-β-carotenoic acid methyl ester (LC: 93%) in 250 ml of methanol and 20 ml of tert.butyl methyl ether was added thereto at room temperature. The mixture was stirred at 60° C. for about 16 hours, which gave a red suspension [tlc (SiO$_2$): R$_f$=0.45; toluene]. The suspension was cooled to 0° C. and 5 ml of acetic acid were added thereto. Then the precipitate was suction filtered, washed with 30 ml of methanol at 0° C., twice with 50 ml, a total of 100 ml, of water at room temperature and again with 50 ml of methanol at 0° C. and dried at 40° C. and 12 mbar. This gave 4.3 g (76%) of 8'-apo-β-carotenoic acid methyl ester as a red powder, m.p. 145°–146° C.; content according to HPLC: 99.7%; UV (cyclohexane with 3% chloroform): 473 nm (log ε=4.97; E=2096), 448 nm (log ε=5.05; E=2515).

Microanalysis: Calc.: C 83.36% H 9.48% Found: C 83.08% H 9.42%

EXAMPLE 32

4'-Apo-β-carotenoic Acid Ethyl Ester (Neurosporaxanthin Ethyl Ester)

1.16 g (2 mmol) of 8'-methoxy-7',8'-dihydro-4'-apo-β-carotenoic acid ethyl ester (HPLC: 96%) in 80 ml of ethanol were placed under argon in a 150 ml round flask. A sodium ethylate solution, prepared by dissolving 140 mg (6 mmol) of sodium in 10 ml of ethanol, was added at room temperature to the resulting red suspension and the mixture was stirred at 40° C. for about 16 hours [tlc (SiO$_2$): R$_f$=about 0.4–0.5; toluene]. Then the mixture was cooled to room temperature, 1 ml (1.05 g, 16 mmol) of acetic acid was added thereto and the mixture was cooled to 0° C. After stirring the suspension at 0° C. for 2 hours it was suction filtered and the filter material was washed with 100 ml of ethanol at −20° C., with 100 ml of water at room temperature and again with 100 ml of ethanol at −20° C. After drying to constant weight under a water-jet vacuum at room temperature there were obtained 800 mg (75% yield) of neurosporaxanthin ethyl ester, m.p. 144°–145° C. (content according to HPLC: 98.7%). UV (n-hexane): 502 nm (log ε=5.09; E=2173), 471 nm (log ε=5.18; E=2857), 450 (log ε=5.06; E=2173), 290 (log ε=4.47; E=563).

Microanalysis: Calc.: C 84.36% H 9.57% Found: C 84.36% H 9.52%

EXAMPLE 33

4'-Apo-β-carotenoic acid ethyl ester (through process from 8'-apo-β-carotenal dimethyl acetal and 1-trimethylsilyloxy-1-ethoxy-2-methyl-1,3-butadiene via 8'-methoxy-7',8'-dihydro-4'-apo-β-carotenoic acid ethyl ester)

4.80 g (10 mmol) of 8'-apo-β-carotenal dimethyl acetal (content according to HPLC: 97%) and 2.60 g (12 mmol) of 1-trimethylsilyloxy-1-ethoxy-2-methyl-1,3-butadiene (content according to GC: 94%) were suspended in 100 ml of tert.butyl methyl ether under argon in a 250 ml round flask equipped with a magnetic stirrer. 70 mg (0.5 mmol, 5 mol %) of anhydrous zinc chloride were added to the suspension at 0° C. and then the mixture was stirred at room temperature for 3 hours, which gave a deep red solution [tlc (SiO$_2$): R$_f$=0.2–0.3; toluene]. Then the solution was poured into 100 ml of water and extracted twice with 100 ml each time, a total of 200 ml, of tert.butyl methyl ether, and washed once with 100 ml of water and once with 100 ml of saturated sodium chloride solution. After drying over anhydrous sodium sulphate the combined organic phases were concentrated and gave 7.3 g of crude 8'-methoxy-7',8'-dihydro-4'-apo-β-carotenoic acid ethyl ester as a deep red, viscous oil. This residue was dissolved in 250 ml of absolute ethanol and the solution was placed in a 350 ml four-necked sulphonation flask equipped with a mechanical stirrer, a thermometer and argon gasification. A sodium ethylate solution, prepared by dissolving 600 mg (26 mmol) of sodium in 40 ml of absolute ethanol, was now added to the solution at room temperature and the mixture was stirred at 45° C. for about 16 hours [tlc (SiO$_2$): R$_f$=about 0.4; toluene]. After cooling to room temperature 2.4 g (40 mmol) of acetic acid were added and the mixture was cooled to 0° C. The mixture was suction filtered and washed twice with 10 ml each time, a total of 20 ml, of ethanol/water (19:1), once with 50 ml of water and a further twice with 10 ml, a total of 20 ml, of ethanol/water (19:1). After drying under a water-jet vacuum at 45° C. and subsequently under a high vacuum at room temperature there were obtained 4.2 g (77% yield) of 4'-apo-β-carotenoic acid ethyl ester as brick-red crystals, m.p. 144° C. and a content according to HPLC of 97.6%. For further purification, the crude product (4.2 g) was digested for about 10 minutes in 120 ml of acetone under argon while stirring at reflux. Then 4 ml of water were added dropwise through the reflux condenser within about 5 minutes and the mixture was cooled slowly to 0° C. and filtered. After washing the filter material with about 20 ml of acetone/water (9:1) at 0° C., with 50 ml of water at room temperature and again with 10 ml of acetone/H$_2$O (9:1) at 0° C. the filter material was dried under reduced pressure at 50° C. and under a high vacuum at room temperature to give 4.03 g (75% yield) of neurosporaxanthin ethyl ester as violet crystals with m.p. 146° C. and a content according to HPLC of 99.4%.

EXAMPLE 34

4'-Apo-β-carotenoic acid ethyl ester (through process from 8'-apo-β-carotenal dimethyl acetal and 1,1-dimethoxy-2-methyl-1,3-butadiene via 8'-methoxy-7',8'-dihydro-4'-apo-β-carotenoic acid methyl ester 4.80 g (10 mmol) of 8'-apo-β-carotenal dimethyl acetal (HPLC: 97%) and 1.95 g (15 mmol) of 1,1-dimethoxy-2-methyl-1,3-butadiene (content according to GC: 99.5%) in 100 ml of tert.butyl methyl ether were placed while gassing with argon in a 200 ml round flask equipped with a magnetic stirrer. 3 drops (about 35 mg, 2.5 mol %) of boron trifluoride etherate were added while stirring to the resulting suspension at 0° C. Thereby, the suspension dissolved within about 30 minutes and a dark red solution formed [tlc (SiO$_2$): R$_f$=about 0.1; toluene]. For the hydrolysis, 20 ml of acetic acid/water (9:1) were added at 0° C. and the mixture was warmed to room temperature and stirred at this temperature for 30 minutes [tlc(SiO$_2$): R$_f$=about 0.25; toluene]. Working-up analogously to Example 33 gave 6.6 g of crude 8'-methoxy-7',8'-dihydro-4'-apo-β-carotenoic acid methyl ester as a deep red, viscous resin. This residue was placed with 200 ml of ethanol in a 350 ml four-necked sulphonation flask equipped with a mechanical stirrer, a thermometer and argon gasification and treated at room temperature with a sodium methylate solution prepared by dissolving 600 mg (26 mmol) of sodium in 90 ml of ethanol. Subsequently, the mixture was stirred at 45° C. for about 16 hours [tlc (SiO$_2$): R$_f$=about 0.5; toluene] and cooled to room temperature, and then 2.4 g (40 mmol) of acetic acid were added dropwise followed by 5 ml of water. Filtration and washing as described in Example 33 gave 4.8 g (89% yield) of 4'-apo-β-carotenoic acid ethyl ester as a red-violet powder, m.p. 144° C.; content according to HPLC: 98.1%. A further purification in acetone/water as described in Example 33 gave 4.44 g (84% yield) of 4'-apo-β-carotenoic acid ethyl ester as violet, fine crystals with m.p. 146°–147° C. and a content according to HPLC of 99.2%.

EXAMPLE 35

4'-Apo-β-carotenoic acid methyl ester (neurosporaxanthin methyl ester; through process from 8'-apo-β-carotenal dimethyl acetal and 1,1-dimethoxy-2-methyl-1,3-butadiene via 8'-methoxy-7',8'-dihydro-4'-apo-β-carotenoic acid methyl ester 4.80 g (10 mmol) of 8'-apo-β-carotenal dimethyl acetal (HPLC: 97%) and 2.20 g (17 mmol) of 1,1-dimethoxy-2-methyl-1,3-butadiene were suspended in 100 ml of tert.butyl methyl ether while gassing with argon in a 300 ml round flask equipped with a magnetic stirrer and treated at 0° C. with 2 drops (about 25 mg, about 2 mol %) of boron trifluoride etherate. After dissolution of the suspension in about 20–30 minutes (tlc control) 20 ml of acetic acid/water (9:1) were added at 0° C. and the mixture was stirred at room temperature for 50 minutes. Working-up as described in Example 33 gave about 7 g of crude 8'-methoxy-7',8'-dihydro-4'-apo-β-carotenoic acid methyl ester as a red, highly viscous oil.

This was suspended in 250 ml of methanol and 20 ml of tert.butyl methyl ether under argon in a 350 ml four-necked sulphonation flask equipped with a mechanical stirrer. A sodium methylate solution, prepared by dissolving 700 mg (30 mmol) of sodium in 50 ml of methanol, was added to the suspension and the mixture was stirred at 50° C. for about 16 hours. Then a solution of 360 mg (15 mmol) of sodium in 15 ml of methanol was added thereto and the mixture was refluxed at about 62° C. for 4 hours [tlc ($SiO_2$): $R_f$=about 0.5; toluene]. The mixture was cooled to 0° C., 3.6 g (60 mmol) of acetic acid were added and the mixture was filtered and washed with 30 ml of methanol at 0° C., twice with 25 ml each time, a total of 50 ml, of water and again with 40 ml of methanol at 0° C. After drying at 45° C. under a water-jet vacuum and at room temperature under a high vacuum there were obtained 4.60 g (88% yield) of 4'-apo-β-carotenoic acid methyl ester as red-violet crystals with m.p. 147°–148° C. and a content according to HPLC of 97.8%. Further purification of these crystals with acetone/water as described in Example 33 gave 4.06 g (78% yield) of 4'-apo-β-carotenoic acid methyl ester as violet crystals with m.p. 150°–151° C. and a content according to HPLC of 99.1%; UV (cyclohexane with 3% chloroform): 509 nm (log ε=5.07; E=2290), 479 nm (log ε=5.16; E=2830), 292 nm (log ε=4.47; E=574).

Microanalysis: Calc.: C 84.32% H 9.44% Found: C 84.07% H 9.30%

EXAMPLE 36

3',4'-Didehydro-β, ψ-carotenoic Acid Ethyl Ester (Torularhodin Ethyl Ester)

800 mg (1.22 mmol) of 4'-methoxy-β,ψ-caroten-16'-oic acid ethyl ester were placed in 20 ml of ethanol in a 100 ml round flask equipped with a magnetic stirrer, a condenser and argon gasification. A sodium ethylate solution, prepared by dissolving 85 mg (3.7 mmol) of sodium in 10 ml of ethanol, was added at room temperature and the mixture was stirred at 50° C. for 18 hours and at 70° C. for 30 minutes [tlc ($SiO_2$): $R_f$=about 0.35; toluene]. Then the mixture was cooled to 0° C., acidified with 0.5 ml of acetic acid, suction filtered, washed with cold water and cold ethanol and dried to constant weight at 35° C. under a high vacuum. This gave 640 mg (88% yield) of torularhodin ethyl ester as a deep violet crystalline powder with m.p. 158°–160° C. and a content of 99.5% according to HPLC. UV (cyclohexane with 3% chloroform): 537 nm (log ε=5.12; E=2240), 503 nm (log ε=5.22; E=2815), 480nm (log ε=5.11; E=2178), 321 nm (log ε=4.58; E=642).

EXAMPLE 37

3',4'-Didehydro-β,ψ-carotenoic Acid Methyl Ester (Torularhodin Methyl Ester)

530 mg (0.79 mmol) of 4'-methoxy-β,ψ-caroten-16'-oic acid methyl ester (content according to HPLC=91.3%) were placed in 20 ml of methanol while gassing with argon in a 50 ml round flask equipped with a magnetic stirrer. A sodium methylate solution, prepared by dissolving 150 mg (6.5 mmol) of sodium in 15 ml of methanol, was added thereto at room temperature and the mixture was stirred at 60° C. for 24 hours [tlc ($SiO_2$): $R_f$=about 0.4; toluene]. Then the mixture was acidified with 5 ml of acetic acid and cooled to 0° C., and the solid filtered off, washed twice with in each case 20 ml, a total of 40 ml, of water and twice with 10 ml, a total of 20 ml, of ice-cold methanol and dried at room temperature under a high vacuum. This gave 435 mg (91% yield) of torularhodin methyl ester as a deep violet, crystalline powder with m.p. 174°–177° C. and a content of 95.3% according to HPLC. UV (cyclohexane with 3% chloroform): 537 nm (log ε=5.11; E=2232), 504 nm (log ε=5.21; E=2824), 480 nm (log ε=5.10; E=2200), 321 nm (log ε=4.57; E=642).

EXAMPLE 38

8'-Apo-β-Carotenoic Acid 1.90 g (3.6 mmol) of 12'-methoxy-11,12'-dihydro-8'-apo-β-caroten-8'-oic acid (HPLC: 88.6%) were dissolved in 80 ml of tetrahydrofuran while gassing with argon in a 150 ml round flask equipped with a magnetic stirrer. 1.83 g (16 mmol, 4.5 eq.) of potassium tert.butylate were added thereto at 0° C. and the mixture was stirred at this temperature for 4 hours [tlc ($SiO_2$): $R_f$=about 0.3–0.4; toluene/ethyl acetate (4:1)]. Then the mixture was poured into water and extracted with 50 ml of ethyl acetate. The extract was washed with 50 ml of water and 50 ml of saturated sodium chloride solution, dried over anhydrous sodium sulphate and filtered. After concentration under reduced pressure there were obtained 1.8 g of residue, which was digested in 25 ml of hot toluene. After cooling to 0° C. over 18 hours the mixture was filtered, washed with a small amount of toluene and dried. This gave 570 mg (36% yield) of 8'-apo-β-carotenoic acid as a dark red powder with m.p. 193°–194° C. and a purity of 97.2% according to HPLC after methylation with diazomethane; UV (cyclohexane with 3% of chloroform): 450 nm (log ε=4.96; E=2100), 263 nm (log ε=4.18; E=350).

EXAMPLE 39

8,8'-Diapocarotene-8,8'-dioic Acid Ethyl Ester (Crocetin Diethyl Ester)

5.91 g (12.7 mmol) of 11,12,11',12'-tetrahydro-12,12'-dimethoxy-8,8'-diapocarotene-8,8'-dioic acid ethyl ester (content according to HPLC 96.1%) were placed in 150 ml of ethanol in a 350 ml four-necked sulphonation flask equipped with a mechanical stirrer, a thermometer and argon gasification. A sodium ethylate solution, prepared by dissolving 920 mg (40 mmol) of sodium in 50 ml of ethanol, was added dropwise thereto at room temperature and the mixture was stirred at room temperature for 20 hours and at 50° C. for 2½ hours [tlc ($SiO_2$): $R_f$=about 0.35; n-hexane/ethyl acetate (4:1)]. After cooling to room temperature 60 ml of acetic acid were added thereto, the mixture was cooled to 0° C. and the precipitate was filtered off and washed three times with 100 ml each time, a total of 300 ml, of water and twice with 50 ml each time, a total of 100 ml, of ethanol at 0° C. After drying (12 mbar at 50° C. and one hour under a high vacuum at room temperature) there were obtained 4.02 g (80% yield) of crocetin diethyl ether as an orange powder with m.p. 204°–210° C. and a content of 96.7% according to HPLC. For analysis, a sample was recrystallized from hot toluene. The sample obtained had a m.p. of 208°–211° C.; content according to HPLC: 97.8%; UV (chloroform): 461 nm (log $\epsilon$=5.04; E=2877), 433 nm (log $\epsilon$=5.07; E=3037), 411 nm (log $\epsilon$=4.87; E=1970).

Microanalysis: Calc.: C 74.97% H 8.39% Found: C 74.72% H 8.45%

EXAMPLE 40

8,8'-Diapocarotene-8,8'-dioic Acid Ethyl Ester (Crocetin Diethyl Ester)

2.18 g (5.2 mmol) of 11,12,11',12'-tetrahydro-12,12'-dimethoxy-8,8'-diapocarotene-8,8'-dioic acid methyl ester (content according to HPLC: 99.7%) were placed in 100 ml of ethanol in a 200 ml four-necked sulphonation flask equipped with a mechanical stirrer, a condenser and argon gasification. A sodium ethylate solution, prepared by dissolving 410 mg (17.8 mmol, 3.5 eq.) of sodium in 65 ml of ethanol, was added dropwise to the mixture at room temperature and the mixture was stirred at room temperature for 16 hours and at 45°–55° C. for 5 hours [tlc (SiO$_2$): R$_f$=about 0.4; n-hexane/ethyl acetate (4:1)]. Then the mixture was cooled to 0° C., 25 ml of acetic acid/water (1:9) were added and the mixture was stirred at 0° C. for 1 hour. The precipitate was filtered off, washed twice with 50 ml each time, a total of 100 ml, of water and twice with 25 ml each time, a total of 50 ml, of ethanol at 0° C. and dried at 12 mbar/40° C. This gave 1.55 g (76% yield) of crocetin diethyl ester as orange-red crystals, m.p. 206°–210° C.; content according to HPLC: 97.6%.

EXAMPLE 41

8,8'-Diapocarotene-8,8'-dioic Acid Methyl Ester (Crocetin Dimethyl Ester)

2.58 g (6.12 mmol) of 11,12,11',12'-tetrahydro-12,12'-dimethoxy-8,8'-diapocarotene-8,8'-dioic acid methyl ester (content according to HPLC: 99.7%) were placed in 50 ml of methanol in a 200 ml four-necked sulphonation flask equipped with a mechanical stirrer, a dropping funnel, a thermometer and argon gasification. A sodium methylate solution, prepared by dissolving 410 mg (18 mmol) of sodium in 45 ml of methanol, was added dropwise to the mixture and the mixture was stirred at 50° C. for about 16 hours [tlc (SiO$_2$): R$_f$=about 0.2; n-hexane/ethyl acetate (4:1) ]. Then the mixture was cooled to 0° C., 25 ml of acetic acid/water (1:9) were added dropwise, the mixture was stirred for 1½ hours, filtered and the solid washed twice with 50 ml each time, a total of 100 ml, of water and twice with 50 ml each time, a total of 100 ml, of methanol at –10° C. After drying at 12 mbar/40° C. and under a high vacuum at room temperature there were obtained 1.95 g (88% yield) of crocetin dimethyl ester as an orange powder with m.p. 212°–219° C. and a content of 97.9% according to HPLC. For the analytical data, a sample was recrystallized from hot toluene. This sample had a m.p. of 219°–222° C.; content according to HPLC: 98.7%; UV (chloroform): 461 nm (log $\epsilon$=4.98; E=2654), 434 nm (log $\epsilon$=5.00), 410 nm (log $\epsilon$=4.82; E=1851).

Microanalysis: Calc.: C 74.13% H 7.92% Found: C 73.93% H 8.02%

EXAMPLE 42

4,4'-Diapocarotene-4,4'-dioic Acid Ethyl Ester 240 mg (10.4 mmol) of sodium were dissolved in 70 ml of ethanol while gassing with argon in a 100 ml round flask equipped with a magnetic stirrer. 1.00 g (1.68 mmol) of 7,8,7',8'-tetrahydro-8,8'-dimethoxy-4,4'-diapocarotene-4,4'-dioic acid ethyl ester (content according to HPLC: 97.8%) was added thereto at room temperature and the mixture was refluxed for about 18 hours [tlc (SiO$_2$): R$_f$=about 0.6; toluene/ethyl acetate (9:1)]. Then the reaction solution was cooled to room temperature and treated with 20 ml of ethanol/acetic acid (9:1). The separated product was filtered off under suction, washed three times with 20 ml each time, a total of 60 ml, of water and three times with 20 ml each time, a total of 60 ml, of ice-cold ethanol and dried at room temperature under a high vacuum. This gave 560 mg (61% yield) of 4,4'-diapocarotene-4,4'-dioic acid ethyl ester as a dark violet powder with m.p. 188°–189° C. and a content of 94.4% according to HPLC. UV (cyclohexane with 3% chloroform): 525 nm (log $\epsilon$=5.12, E=2524); 490 nm (log $\epsilon$=5.21; E=3154), 461 nm (log $\epsilon$=5.07; E=2287), 313 nm (log $\epsilon$=4.56; E=690).

EXAMPLE 43

4,4'-Diapocarotene-4,4'-dioic Acid Methyl Ester 1.00 g (43 mmol) of sodium was dissolved in 120 ml of methanol while gassing with argon in a 250 ml round flask equipped with a magnetic stirrer. 1.20 g (2.17 mmol) of 7,8,7',8'-tetrahydro-8,8'-dimethoxy-4,4'-diapocarotene-4,4'-dioic acid methyl ester (content according to HPLC: 98.7%) were added thereto at room temperature and the mixture was refluxed for about 16 hours [tlc (SiO$_2$): R$_f$=about 0.6; toluene/ethyl acetate (9:1)]. The suspension was then cooled to room temperature, treated with 20 ml of methanol/glacial acetic acid (9:1) and, after cooling to 0° C., filtered. The filter material was washed three times with 20 ml each time, a total of 60 ml, of water and three times with 20 ml each time, a total of 60 ml, of ice-cold methanol and dried at room temperature under a high vacuum. This gave 0.60 g (55% yield) of 4,4'-diapocarotene-4,4'-dioic acid methyl ester as a red powder with m.p. 201° C. and a content of 97.9% according to HPLC. UV (cyclohexane with 3% chloroform): 525 nm (log $\epsilon$=5.18, E=3089), 491 nm (log $\epsilon$=5.24; E=3547), 462 nm (log $\epsilon$=5.08; E=2440), 313 nm (log $\epsilon$=4.61; E=834).

The above description was provided to aid in understanding the invention. Upon reading the entire specification, however, certain variant embodiments will become obvious to the skilled artisan. These variations are to be considered with the scope and spirit of the invention which is to only be limited by the claims that follow and their equivalents.

What is claimed is:

1. A process for manufacturing a compound of formula:

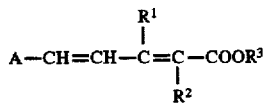

or

-continued

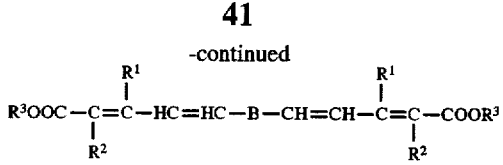 I'''

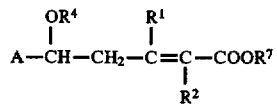 IV' or

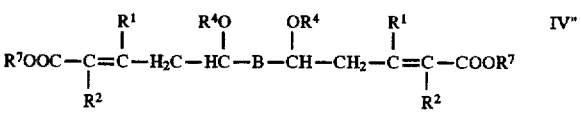 IV'' wherein

A is a monovalent conjugated polyene group or a methyl-substituted, monovalent conjugated polyene group, B is a bivalent conjugated polyene group or a methyl-substituted, bivalent conjugated polyene group, $R^1$ and $R^2$ each independently is hydrogen or methyl, and $R^3$ is hydrogen or $C_{1-6}$-alkyl, with the —CH=CH—C($R^1$)=C($R^2$)—COOR$^3$ group(s) in each case being situated in the terminal position(s) of the conjugated chain of group A or B, which process comprises:

(A) reacting a compound of formula:

 II' or

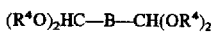 II'' wherein

A and B are as above, with the —CH(OR$^4$)$_2$ group(s) being situated in the terminal position(s) of the conjugated chain of group A or B, and wherein A, B, $R^1$, $R^2$ and $R^4$ are as above, with the —CH(OR$^4$)—CH$_2$C($R^1$)=C($R^2$)COOR$^7$ group(s) being situated in the terminal position(s) of the conjugated chain of group A or B, and $R^7$ is $C_{1-6}$-alkyl, hydrogen, 2-hydroxyethyl or 3-hydroxy-n-propyl;

(B) cleaving off the $R^4$OH group from the compound formula IV' or IV'' under strong basic conditions; and (C) where there is a difference between groups —COOR$^7$ and —COOR$^3$, converting group —COOR$^7$ to group —COOR$^3$.

2. The process according to claim 1, wherein the reacting involves a compound of the formula:

 II wherein

R is a group (a), (b) or (c)

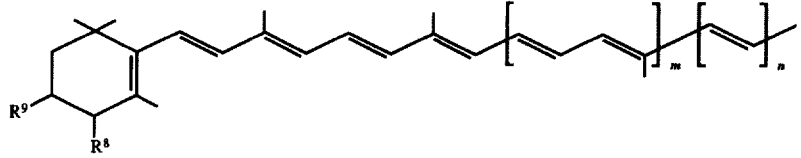

(a)

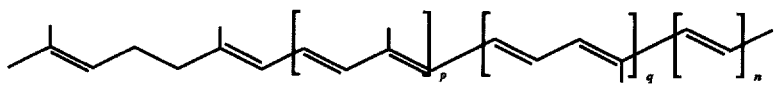

(b)

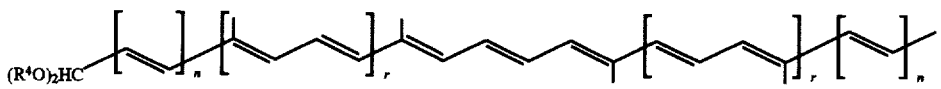

(c)

$R^4$ is $C_{1-6}$-alkyl, with a compound of formula:

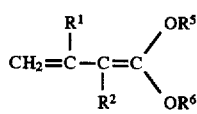 III wherein $R^1$ and $R^2$ are as above, and $R^5$ is $C_{1-6}$-alkyl and $R^6$ is $C_{1-6}$-alkyl or tri($C_{1-6}$-alkyl)silyl, or $R^5$ and $R^6$ both are tri($C_{1-6}$-alkyl)silyl, or $R^5$ and $R^6$ together form 1,2-ethylene or 1,3-trimethylene, in the presence of a Lewis acid, and where a compound of formula III in which $R^5$ and $R^6$ both are $C_{1-6}$-alkyl or both are tri($C_{1-6}$-alkyl)silyl or together form 1,2-ethylene or 1,3-trimethylene is used, subsequently hydrolyzing the compound formed, so as to form in all cases a compound of the formula:

in which $R^4$ is $C_{1-4}$-alkyl, $R^8$ and $R^9$ each independently is hydrogen, a hydroxy group, a protected hydroxy group, an oxo group or a protected oxo group, m is 0, 1, 2, 3 or 4, n is 0 or 1, p is 0, 1 or 2, q is 0, 1, 2 or 3, and r is 0, 1 or 2, which is converted after carrying out the multistage process defined in claim 1 into the corresponding product of formula:

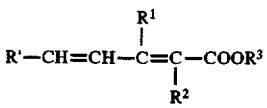 I wherein R' is as above for R, with the group ($R^4$O)$_2$HC— being replaced by the $R^3$OOC—C($R^2$)=C($R^1$)—HC=HC— group when R' is group (c).

3. The process according to claim 2, wherein R is a group (a) and a protecting group is present, the process further comprising cleaving the protecting group.

4. The process according to claim 1, wherein the compound of formula II' or II" is reacted with a compound of formula III in an organic solvent at temperatures in the range of from about −40° C. to about 100° C. in the presence of a Lewis acid selected from the group consisting of zinc chloride, zinc bromide, titanium tetrachloride, lithium perchlorate, boron trifluoride etherate, and iron(III) chloride.

5. The process according to claim 4, wherein the organic solvent is selected from the group consisting of lower aliphatic hydrocarbon, cyclic hydrocarbon, lower, halogenated aliphatic hydrocarbon, lower aliphatic ether, cyclic ether, lower aliphatic nitrile, and aromatic compounds.

6. The process according to claim 5, wherein the organic solvent is selected from the group consisting of n-pentane, n-hexane, cyclohexane, methylene chloride, chloroform, diethyl ether, tert.butyl methyl ether, tetrahydrofuran, acetonitrile and toluene, and the reaction of the compound of formula II' or II" with the compound of formula III is effected in the temperature range of about −20° C. to room temperature.

7. The process according to claim 1, wherein the strong base for the cleavage of the alcohol $R^4OH$ from the compound of formula IV' or IV" is an alkali metal alcoholate or an alkali metal hydride.

8. The process according to claim 7, wherein the cleavage of the alcohol $R^4OH$ is carried out in a solvent selected from the group consisting of an alcohol, an aliphatic ether, a cyclic ether, an aliphatic ester, an aromatic, an aliphatic hydrocarbon, a lower halogenated aliphatic hydrocarbon and a mixture of an alcohol with another solvent referred to above.

9. The process according to claim 7, wherein the cleavage of the alcohol $R^4OH$ is carried out using a sodium alkoxide as the base and the corresponding alkanol as the solvent at temperatures between room temperature and the reflux temperature of the respective reaction mixture.

* * * * *